(12) United States Patent
Deland

(10) Patent No.: US 12,390,212 B2
(45) Date of Patent: Aug. 19, 2025

(54) ACHILLES TENDON REPAIR DEVICE

(71) Applicant: Jonathan T. Deland, New York, NY (US)

(72) Inventor: Jonathan T. Deland, New York, NY (US)

(*) Notice: Subject to any disclaimer, the term of this patent is extended or adjusted under 35 U.S.C. 154(b) by 0 days.

(21) Appl. No.: 18/525,075

(22) Filed: Nov. 30, 2023

(65) Prior Publication Data
US 2024/0090892 A1  Mar. 21, 2024

Related U.S. Application Data

(63) Continuation of application No. 17/443,723, filed on Jul. 27, 2021, now Pat. No. 11,896,215.
(Continued)

(51) Int. Cl.
*A61B 17/04* (2006.01)
*A61B 17/11* (2006.01)

(52) U.S. Cl.
CPC ...... *A61B 17/0469* (2013.01); *A61B 17/0482* (2013.01); *A61B 17/0487* (2013.01);
(Continued)

(58) Field of Classification Search
CPC ............ A61B 17/0469; A61B 17/0482; A61B 17/1146; A61B 17/0483; A61B 2017/0472; A61B 2017/1103
See application file for complete search history.

(56) References Cited

U.S. PATENT DOCUMENTS 4,465,065 A  8/1984 Gotfried
4,592,346 A * 6/1986 Jurgutis ................. A61B 17/10
                                                                411/457
(Continued)

FOREIGN PATENT DOCUMENTS

| CN | 107736904 A | 2/2018 |
|---|---|---|
| WO | WO-2006/047563 A2 | 5/2006 |
| WO | WO-2022/027029 A1 | 2/2022 |

OTHER PUBLICATIONS

Extended European Search Report for EP Application No. 21851352.1 dated Jun. 5, 2024.
(Continued)

*Primary Examiner* — Alexander J Orkin
(74) *Attorney, Agent, or Firm* — Stephen J. Kenny; Nicole A. Bustos-Pomerantz; Foley Hoag LLP

(57) ABSTRACT

An Achilles tendon repair device comprises a handle for physician gripping and base having a first set of tendon rods disposed in an arcuate or U-shaped pattern about the base to engage the posterior surface of the tendon and impart a contour, or drape, the tendon in the posterior-anterior plane to increase the surface area for suturing. A second set of suture guide rods extend from the sides of the base and are spaced apart to allow insertion of suture needles along the entire length of the suture guide rods, and at any angle. A suture needle housing guide can be slidingly attached to the suture guide rods and includes sidewalls with predefined suture holes/angles. An adjustable clamping arm can engage the tendon's posterior surface such that the device grasps the tendon on both the anterior and posterior tendon surfaces simultaneously, while increasing posterior-anterior plane surface area to facilitate suturing.

21 Claims, 38 Drawing Sheets

Related U.S. Application Data

(60) Provisional application No. 63/057,036, filed on Jul. 27, 2020.

(52) U.S. Cl.
CPC ... *A61B 17/1146* (2013.01); *A61B 2017/0472* (2013.01); *A61B 17/0483* (2013.01); *A61B 2017/1103* (2013.01)

(56) References Cited

U.S. PATENT DOCUMENTS

| | | | |
|---|---|---|---|
| 5,078,719 | A | 1/1992 | Schreiber |
| 5,098,383 | A | 3/1992 | Hemmy et al. |
| 5,496,341 | A | 3/1996 | Sauer et al. |
| 5,507,755 | A | 4/1996 | Gresl et al. |
| 5,800,544 | A * | 9/1998 | Demopulos ........... A61F 2/0811 606/53 |
| 5,830,232 | A | 11/1998 | Hasson |
| 5,931,869 | A | 8/1999 | Boucher et al. |
| 6,036,700 | A | 3/2000 | Stefanchik et al. |
| 6,129,729 | A | 10/2000 | Snyder |
| 6,200,327 | B1 | 3/2001 | Assal |
| 6,322,571 | B1 | 11/2001 | Adams |
| 7,615,062 | B2 | 11/2009 | Deland |
| 8,834,339 | B2 | 9/2014 | Hannoun-Levi et al. |
| 9,622,741 | B2 | 4/2017 | Levine |
| 9,629,622 | B2 | 4/2017 | Deland |
| 11,896,215 | B2 | 2/2024 | Deland |
| 2002/0052602 | A1 | 5/2002 | Wang et al. |
| 2004/0073235 | A1* | 4/2004 | Lund ................ A61F 2/0045 606/151 |
| 2004/0102788 | A1 | 5/2004 | Huebner et al. |
| 2006/0069397 | A1 | 3/2006 | Nobles et al. |
| 2006/0149250 | A1 | 7/2006 | Castaneda et al. |
| 2009/0149861 | A1 | 6/2009 | Brodsky et al. |
| 2010/0076467 | A1* | 3/2010 | Yasuda ............ A61B 17/115 606/153 |
| 2014/0228898 | A1 | 8/2014 | Gordon |
| 2016/0242771 | A1* | 8/2016 | Weinstein ........... A61B 17/842 |
| 2017/0367692 | A1 | 12/2017 | Deem et al. |
| 2018/0036002 | A1 | 2/2018 | Chen et al. |
| 2018/0221653 | A1* | 8/2018 | Kim ................ A61N 1/0556 |
| 2022/0022865 | A1 | 1/2022 | Deland |
| 2024/0090892 | A1 | 3/2024 | Deland |

OTHER PUBLICATIONS

International Preliminary Report on Patentability and Written Opinion for PCT/US2005/038490, dated Jun. 10, 2008.
International Search Report and Written Opinion for International Application No. PCT/US2021/071002 dated Oct. 20, 2021.

* cited by examiner

ACHILLES TENDON REPAIR DEVICE

CROSS REFERENCE TO RELATED APPLICATIONS

This application is a Continuation of U.S. patent application Ser. No. 17/443,723, filed on Jul. 27, 2021, which claims the benefit under 35 USC 119 of U.S. Provisional Application No. 63/057,036, filed Jul. 27, 2020, each application is hereby incorporated by reference in its entirety.

BACKGROUND OF THE DISCLOSED SUBJECT MATTER

Field of the Disclosed Subject Matter

The disclosed subject matter relates to a device and method for tendon repair. Particularly, the present disclosed subject matter is directed towards a device and method for improved positioning of the Achilles tendon, and suturing thereof.

Tendon rupture is a debilitating event that limits motion and can cause pain. Rupture can result from overexertion, trauma, and age-related degeneration, among other causes. Surgical repair of the ruptured tendon is typically required; tendinous tissue has poor wound-healing properties, and the torn ends of the tendon separate from one other due to contraction of the unrestrained muscle attached to one tendon end.

Surgical repair of a ruptured tendon is typically performed by putting one or more sutures through each torn end and then sewing the complementing sutures to one another, thereby winching the torn ends together and restoring the connected muscle to its normal resting length. Two risks of tendon repair include inadequate strength of the repair and potential soft tissue problems from surgical exposure. Accordingly, it would be best if a tendon could be repaired through a small incision but with a strong repair. With a small incision, the needles used to advance the sutures through the tendon may be advanced manually, without any guides, but this practice risks placing the sutures unevenly, so that the tendon's natural geometry and strength are not restored, and the repair is weak.

One approach, described in U.S. Pat. No. 6,200,327 to Assal, provides a two-piece guide member with aligned channels in each piece, the entirety of this disclosure is hereby incorporated by reference. The aligned channels allow a user to advance a loaded needle horizontally through the tendon in a precise and repeatable fashion. However, the structure of the Assal device necessarily limits each suture to just one pass through the tendon; this results in a potentially weak stitch that provides a minimum of surface area for the suture to engage the tendon. Another known device is disclosed in U.S. Pat. No. 7,615,062 which provides an oblique suture needle guide path, the entirety of this disclosure is hereby incorporated by reference.

Minimal incision Achilles tendon repair has been documented to be a viable technique with the advantage of a significantly smaller incision. This can make for less wound problems, a known complication of Achilles surgery. It can also make for shorter operating room time and less trauma to the tissues. However, it does have a disadvantage. At the location where the repair sutures are being placed, the surgeon cannot see the tendon. The surgeon is unable to verify that the needles are going into the tendon rather than the tissue above the tendon or tissue below the tendon. The surgeon is also unable to verify that the suture construct is capturing adequate tendon tissue for a strong repair. Targeting failure or capturing inadequate tissue makes for a failed or weaker repair. Although not commonly publicized, surgeons have had problems with missing the tendon or inadequately capturing the tendon with the needles used for the repair.

There thus remains a need for a device and operating method that can locate, and adjust the shape or contour in of the tendon for the surgeon—particularly in the posterior to anterior (PA) plane as well as the Medial-Lateral (ML) plane.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes an Achilles tendon repair device comprising: a handle, then handle including a base; a first set of rods extending from the base, at least one rod of the first set of rods configured to engaged the posterior surface of the tendon; a second set of rods extending from the base, the second set of rods including at least one pair of rods extending parallel to each other and spaced from the first set of rods.

In some embodiments, the first set of rods includes four rods equidistantly spaced from each other, and can be distributed in an arcuate pattern about the base.

In some embodiments, the first set of rods includes a first rod, a second rod, a third rod and a fourth rod: wherein the first rod and fourth rod are disposed proximate an anterior edge of the base, and the second rod and third rod are disposed proximate a posterior edge of the base.

In some embodiments, at least one rod of the first set of rods is inserted into the paratenon section of the tendon.

In some embodiments, the first set of rods includes four rods, with each rod configured to engage the Achilles tendon and drape the tendon into a generally arcuate shape in the posterior-anterior plane.

In some embodiments, the second set of rods includes two pairs of rods, a first pair disposed proximate a lateral edge of the base, a second pair disposed proximate a medial edge of the base.

In some embodiments, the second set of rods includes two pairs of rods, at least one pair of the second rods being aligned about an axis extending in the posterior-anterior plane.

In some embodiments, the second set of rods includes two pairs of rods, at least one pair of the second rods being spaced apart to define a gap therebetween, the gap extending along the entire length of the rods.

In some embodiments, the second set of rods includes two pairs of rods, at least one pair of the second rods being spaced apart to define a gap therebetween, the gap sized to receive a suture needle.

In some embodiments, the second set of rods includes two pairs of rods, at least one pair of the second rods being spaced apart to define a gap therebetween, the gap sized to receive a suture needle at any location along the length of the rods.

In some embodiments, the second set of rods includes two pairs of rods, at least one pair of the second rods being spaced apart to define a gap therebetween, the gap sized to receive a suture needle at an angle perpendicular to the rods.

In some embodiments, the second set of rods includes two pairs of rods, at least one pair of the second rods being spaced apart to define a gap therebetween, the gap sized to receive a suture needle at an angle acute to the rods.

In some embodiments, the first set of rods and second set of rods are of equivalent length.

In some embodiments, the first set of rods are fixedly attached to the base.

In some embodiments, the second set of rods are fixedly attached to the base.

In accordance with another aspect of the disclosure, an Achilles tendon repair device is provided comprising: a handle, then handle including a base; a first set of rods extending from the base, at least one rod of the first set of rods configured to engaged a posterior surface of the tendon; a second set of rods extending from the base, the second set of rods including at least one pair of rods extending parallel to each other and spaced from the first set of rods; and a suture needle housing guide, the suture needle housing guide configured to be slidingly attached to the second set of rods.

In some embodiments, the suture needle housing guide is configured as a generally rectangular structure with opposing sidewalls, each sidewall including at least one aperture for receiving a suture needle.

In some embodiments, the second set of rods includes four rods, the suture needle housing guide including four ports for receiving each of the four rods.

In some embodiments, the suture needle housing guide includes an viewing window on the posterior surface.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 15-18C are depictions of exemplary suture patterns for repair of the Achilles tendon using the device disclosed herein; FIGS. 15-17 are side and top views, FIG. 18 is a top view.

DETAILED DESCRIPTION OF AN EXEMPLARY EMBODIMENT

Reference will now be made in detail to exemplary embodiments of the disclosed subject matter, an example of which is illustrated in the accompanying drawings. The method and corresponding steps of the disclosed subject matter will be described in conjunction with the detailed description of the system.

Figure 1:
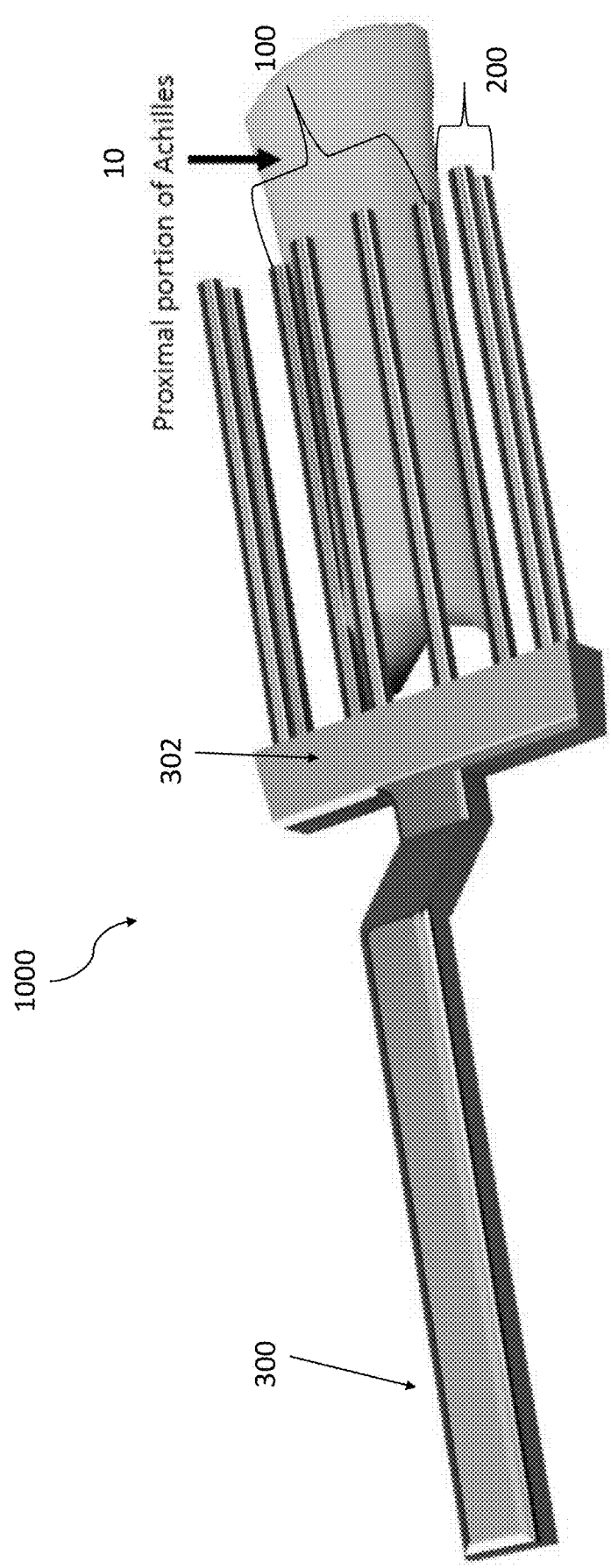
FIG. 1 is a schematic representation of perspective view of an exemplary embodiment of an Achilles tendon repair device, including a partial depiction of a ruptured tendon, in accordance with the disclosed subject matter.
Figure 2:
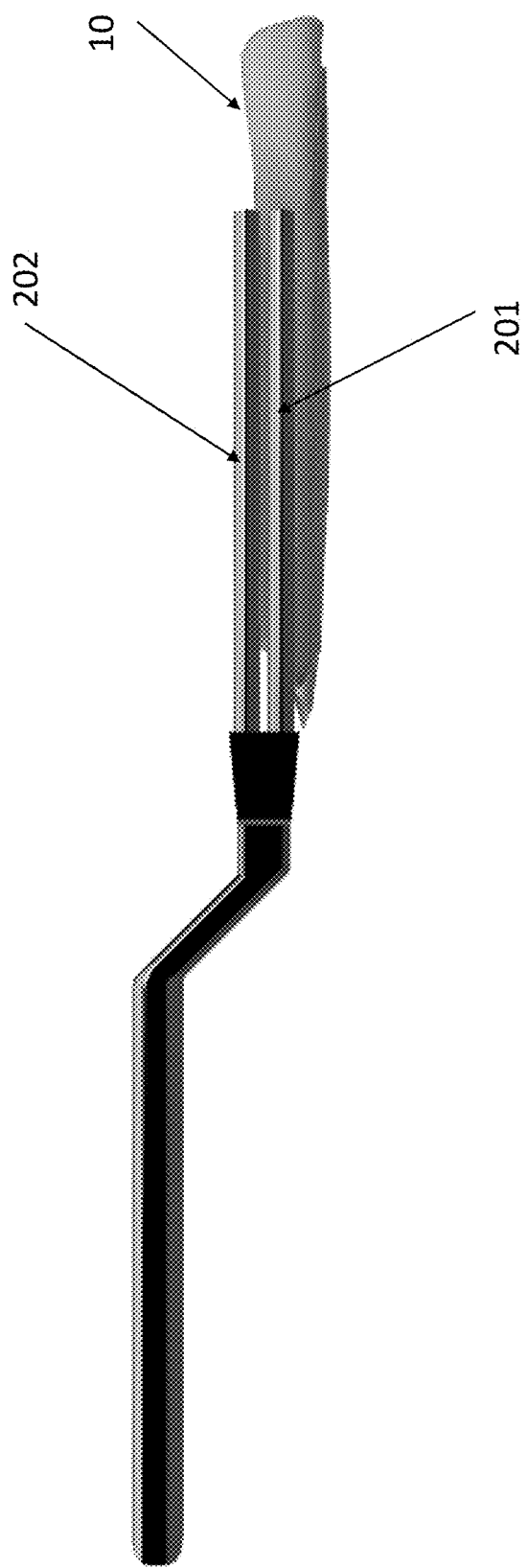
FIG. 2 is a left side view of the exemplary embodiment shown in FIG. 1.
Figure 3:
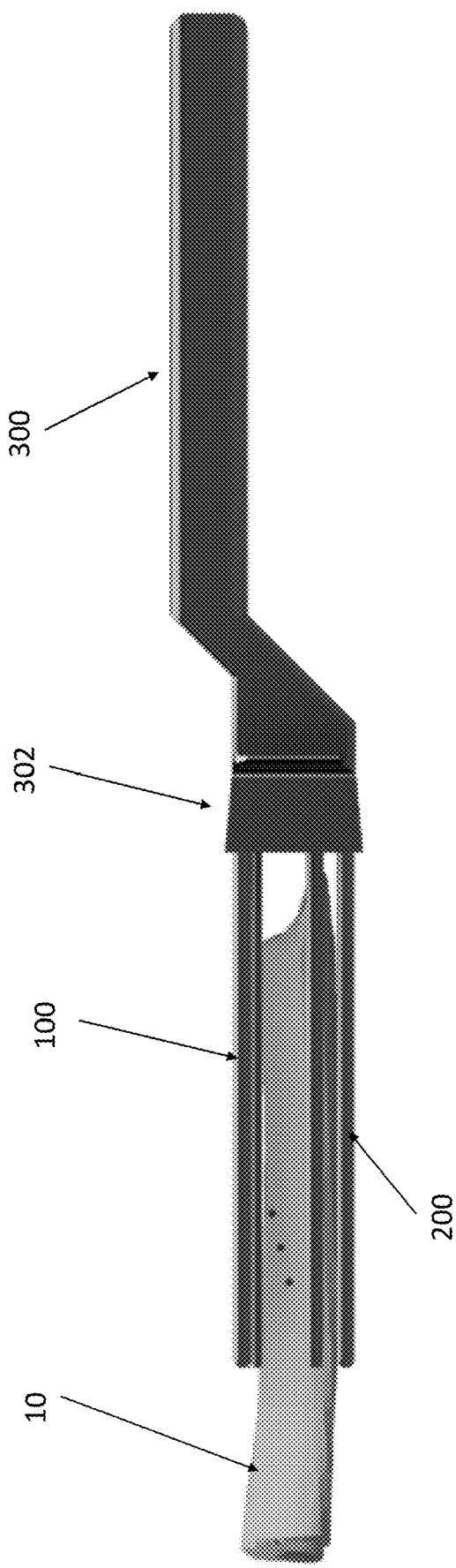
FIG. 3 is a right side view of the exemplary embodiment shown in FIG. 1.

The methods and systems presented herein may be used for minimally invasive Achilles tendon repair. For purpose of explanation and illustration, and not limitation, an exemplary embodiment of the system in accordance with the disclosed subject matter is shown in FIG. 1 and is designated generally by reference character 1000. Similar reference numerals (differentiated by the leading numeral) may be provided among the various views and Figures presented herein to denote functionally corresponding, but not necessarily identical structures.

As shown in FIG. 1, the system 1000 generally includes a first set of elongated members or rods 100, a second set of elongated members/rods 200, and a handle 300. It is to be understood that the geometry of these elongated members can vary (e.g. cylindrical, triangular, faceted/chamfered edges, curved or planar sides, etc.) but for convenience will be referred throughout this disclosure as "rods".

In accordance with an aspect of the present disclosure, the rod(s) target the tendon and have direct contact over the posterior and/or anterior (e.g., when the clamping member of FIGS. 19-38 in included) aspect of the Achilles tendon. This is beneficial during surgery as this is the plane that the surgeon looks along (with the surgeon only able to see the skin which covers the tissue with the tendon, and not the tendon itself because of the small incision). The patient can be positioned in a prone position with the stomach on the table and the back of the calf (known as the posterior aspect) facing the surgeon. The surgeon faces the posterior calf with the posterior Achilles underneath the posterior skin and the anterior aspect of the Achilles, and finally the anterior calf, facing the table.

This posterior to anterior plane is particularly important when placing sutures in the proximal Achilles tendon in the minimal incision surgery. In all Achilles repair surgeries, sutures must be placed in the proximal Achilles tendon to tie down to sutures at the distal Achilles tendon, or less commonly, to the calcaneus. Going from distal to proximal the Achilles tendon becomes wider in the medial-lateral plane but thinner in the posterior-anterior ("PA") plane. In that plane the tendon can become only several millimeters thick. Unfortunately it is this PA plane which is important for targeting. Because needles must be put in from the medial and lateral sides in a minimal incision Achilles repair, targeting the thinner PA proximal tendon is a challenge. When the needles are placed in the proximal Achilles, they can pass too anteriorly or too posteriorly, missing the relatively thin tendon.

Unlike conventional repair devices, the present disclosure includes internal instrumentation to drape the tendon in a manner to give a good target area. A bigger target area would be most helpful as this reduces the chance of missing or just grazing the tendon, resulting in an ineffective suture. Additionally, the present device can manipulate the shape of the tendon to provide a bigger PA distance between the separate needle paths, which become the location of the sutures. This larger distance between needle paths allows for more tendon fibers to be engaged/grabbed by the suture construct. Accordingly, the inner rods are designed to target the tendon and bending or draping it to effectively create a larger target area which results in more reliable targeting and a suture construct with better pull out strength.

In accordance with another aspect of the disclosure, whereas conventional Achilles repair devices have dedicated/fixed channels to limit suture needle angles, the device allows for a greater range of angles of orientation for the suture needles. This "open" guide for the suture needles reduces the amount of elongation of the tendon, and thus reduces the formation of gaps in the repaired tendon—which can lead to tendon failure (or re-rupture). Elongation of the tendon can present a significant issue in that a muscle tendon construct works maximally if proper tension is maintained, so elongation of the repair lessens the proper tension of the repair and therefore makes for less long-term efficiency or full function of the muscle. The open suture needle guide disclosed herein repairs with less risk of elongation and allows for a more aggressive or earlier rehabilitation and less potential loss of efficiency of the muscle tendon unit.

The elongation of the repair in minimal incision surgery is likely related to poor targeting or poor capture of the tendon tissue by the suture construct. Fortunately, poor targeting and poor capture of tendon tissue can be addressed by changes in the inner structure of the repair device, e.g. with instrumentation immediately adjacent to the Achilles tendon in the presently disclosed device.

In some embodiments, the inner instrumentation can lie under the skin and in the paratenon. This instrumentation is completely open in the PA plane, thereby providing full control of the device in this plane. Placing a rod or solid arm in the PA plane adjacent to the Achilles tendon allows for control and holding the tendon for targeting in that plane. The rod or arm can be placed in the paratenon immediately adjacent to the Achilles tendon posteriorly. The handle of the device can be lifted to push the rod or arm against the posterior surface of the Achilles tendon, locating the tendon for the surgeon in the PA plane. Needles can be placed from the side(s) so as to target the tissue immediately underneath/ anterior the rod—i.e. the tendon. Needles could be placed at different distances from the rod in PA plane to pass through the tendon at different locations. The needle paths can also be different in the proximal/distal planes as well. This technique provides sufficient separation of the suture paths in two planes and maximizes the pull out strength of the tendon suture construct.

The interior instrumentation can also consist of medial and lateral rod(s) within the paratenon. These rods can be oriented on the device so as to be just anterior to the tendon and at an appropriate width apart so neither rod extends over the medial or lateral extent of the tendon. These two rods can manipulate the shape of the tendon to drape the tendon into more of an upside down U-shape. The sides of this upside down U-shape will be the larger targeting areas for the tendon on the medial and lateral sides. These target areas are larger than the more regularly flattened out Achilles tendon at this location. The top rods can locate the most posterior aspect of the tendon, and the two side rods will serve to drape the tendon into a more upside down U-shape, the top of which is the most posterior surface of Achilles. The sides are the larger target areas for the medial lateral needles, and the larger target areas will allow for more PA distance between the needle paths. The rods/arms will therefore make for more certain capture of the tendon and a stronger suture construct.

First Set of (Tendon or Internal) Rods (100)

Figure 4:
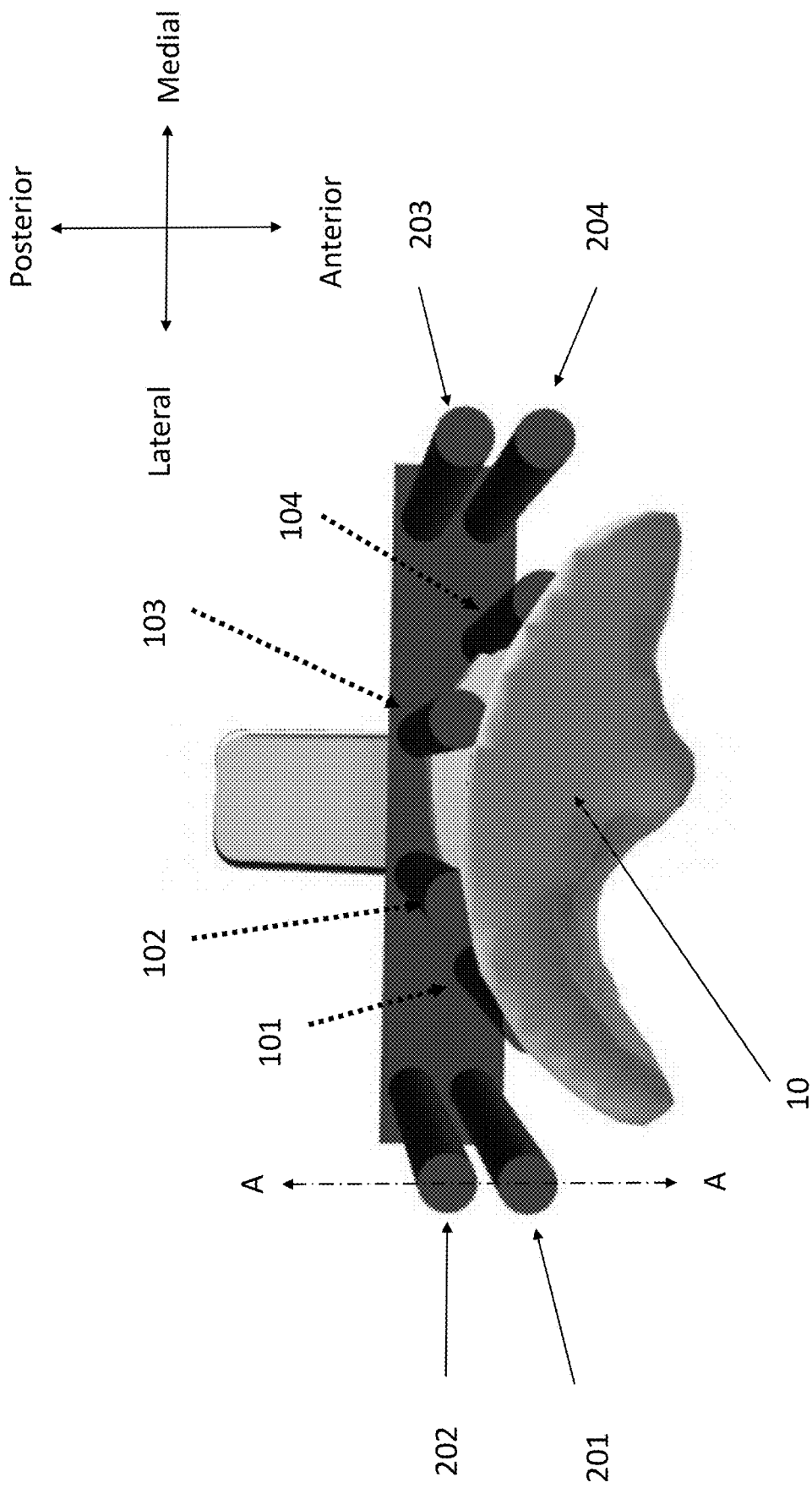
FIG. 4 is an axial view of the exemplary embodiment shown in FIG. 1.

Referring to the exemplary embodiment shown in FIG. 1, a first set of rods 100 are disposed over the proximal portion of the Achilles tendon 10 (the distal portion connected to the patient's heel is not shown for clarity). In the embodiment shown, the first set of rods 100 include four rods 101-104 (as best shown in FIG. 4) that extend both across the lateral-medial plane of the patient as well as the posterior-anterior plane of the patient. The first set of rods 101-104 can be discrete members that are each attached to the base 302. The rods 101-14 can be equidistantly spaced from each other, with uniform gaps/space therebetween, or positioned in a pattern (e.g. inner rods 102-103 can be positioned closer together than they are to rods 101, 104, respectively). As shown in FIGS. 1 and 4, the rods 100 can be configured in an arc shape or curvilinear spacing (e.g. parabolic) to form a semi-circle or upside down U-shape. In some embodiments the first and fourth rods 101, 104 are disposed proximate an anterior edge of the base 302, and the second and third rods 102, 103 are disposed proximate a posterior edge of the base.

In some embodiments, the spacing between rods 100, and/or the radius of curvature of the rods (in the aggregate) can be adjusted to provide a range of settings to accommodate patients of varying size. For example, the amount of curvature exhibited by the rods 100 (and thus imparted to the Achilles tendon) can be adjusted by shifting or sliding the rods 100 within tracks formed in the base 302 that lockingly receive the proximal end of the rods 100. Additionally or alternatively, each of the rods 100 can articulate independently of the other rods. Thus, the rods 100 can be adjusted in the posterior-anterior plane, as well as the medial-lateral plane; independently or simultaneously. In some embodiments a wheel or gear can be included in the handle 300 that allows a physician to gradually adjust the relative positioning of the inner tendon rods 100. For example, rotation of the wheel in a first (e.g. clockwise) direction can bring the innermost rods 102 and 103 in closer proximity (in the posterior plane, as well as the medial-lateral plane, independently or simultaneously) to each other; rotation of the wheel in a second direction can displace the outer rods 101, 104 further in an anterior direction to increase the draping effect on the tendon.

Figure 5:
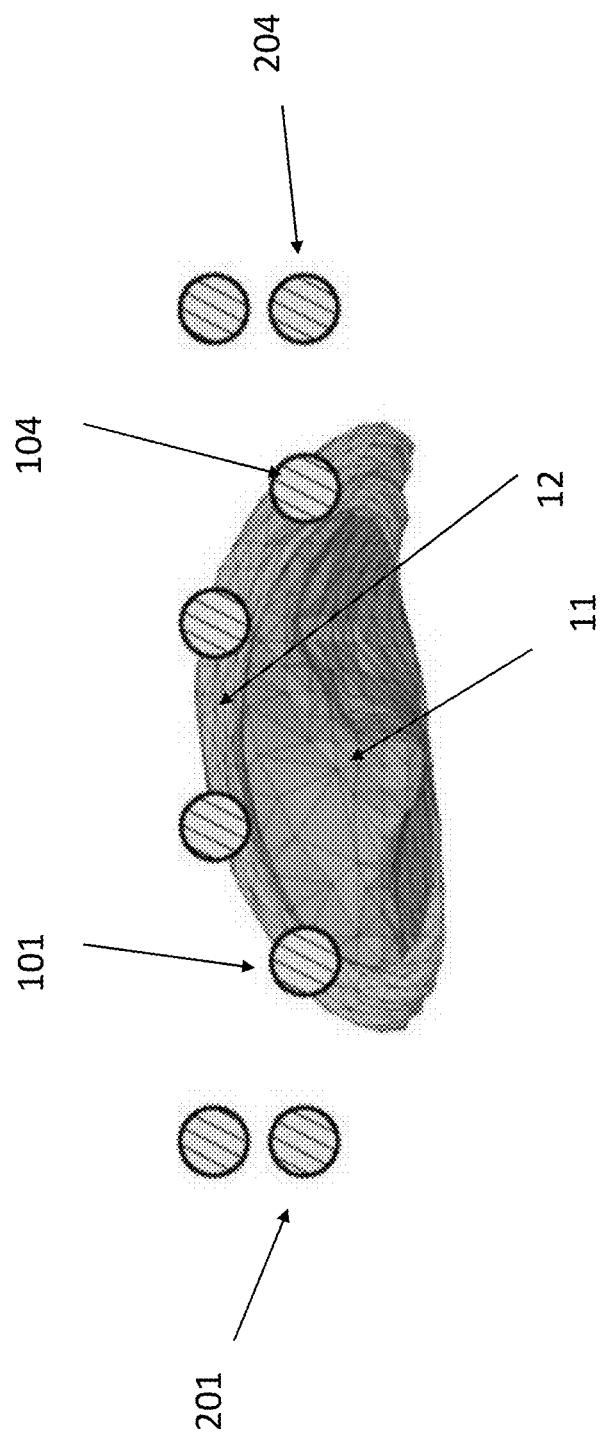
FIG. 5 is a cross-sectional view of the exemplary embodiment shown in FIG. 1.
Figure 6:
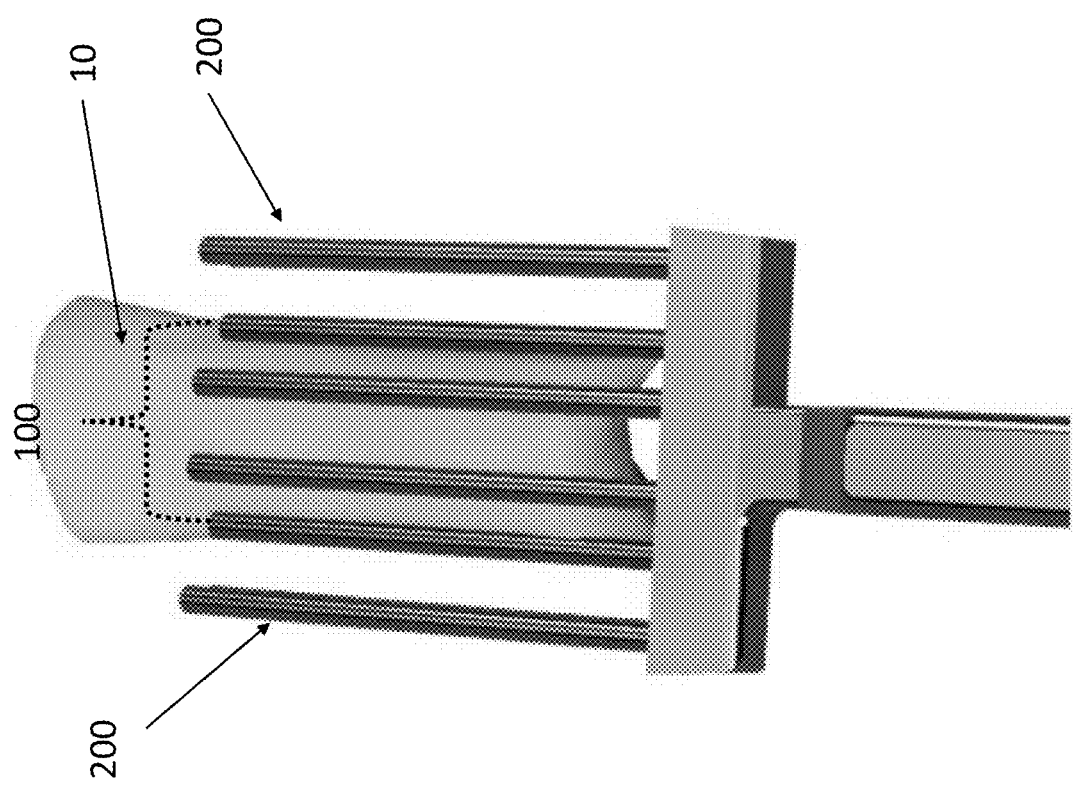
FIG. 6 is a top view of the exemplary embodiment shown in FIG. 1.

As described above, at least one of the first set of rods 100 engages/contacts the posterior surface of the Achilles tendon, in some embodiments each of the first set of rods 100 contacts the posterior surface of the Achilles tendon 10. As shown, the first 101 and fourth 104 rod can contact the Achilles tendon on the medial and lateral sides of the patient's leg, respectively, while the two inner rods 102-103 contact the Achilles tendon proximate an apex (when the tendon is bent/draped into the U-shape as shown) of the posterior surface. In some embodiments, at least one of the first set of rods 100 is inserted under the skin and in the paratenon section 12 of the tendon 11, as shown in the cross-sectional view of FIG. 5. The distal end of the rods 100 can have a tapered tip to facilitate insertion into the paratenon section 12 and displacing the outer sheath from the tendon 11.

The rods 100 direct contact with the Achilles tendon on the posterior surface provides sufficient pressure to:
 i. provide confirmation (e.g. visual, tactile and/or haptic) to the physician that the tendon has been properly identified and engaged;
 ii. prevent the tendon from retracting proximally up the patient's leg—which can introduce errors/gaps when inserting sutures;
 iii. manipulate the shape or contour of the tendon by wrapping or bending the tendon in the posterior-anterior plane into a generally inverted U-shape, to increase the surface area available for inserting sutures.

Although the exemplary embodiment shown depicts the first set of rods 100 as including four rods, additional (or fewer) rods can be employed to accommodate a range of patient sizes/needs. Also, the exemplary embodiment depicts uniformly shaped rods having a fixed length and permanently attached to the base 302, however alternative configurations can be employed including rods of different shapes/sizes/lengths; removable/replaceable rods; and rods of varying length (e.g. telescopingly extendable/retractable). The rods can have a uniform diameter across all rods, or alternatively, have select rods (e.g. central rods 102, 103) can be formed with a different (e.g. larger) diameter than peripheral rods 101, 104.

For example, FIGS. 8-11 depict alternative configurations of the first set of inner rods 100 where, a single inner rod 100 is provided which contacts the upper most surface of the tendon, or apex, when the tendon is draped in the posterior-anterior plane. In the embodiment shown in FIG. 9, two additional rods 101, 103 can be provided to engage the tendon on the medial and lateral sides, respectively. These rods can be formed with an arcuate (non-cylindrical) shape so that a concave inner surface of the rods engage the tendon to enhance the degree of curvature or draping imparted onto the tendon, thereby maximizing the surface area for suture needle targeting. Also, as shown, the rod 102 positioned at the apex of the tendon can have a larger surface area than the medial and lateral rods 101, 103 to increase contact and force exerted on the tendon. It should be noted that the device disclosed herein alters (or stretches/drapes) the tendon in the posterior-anterior plane and simultaneously alters (or narrows) the tendon in the medial-lateral plane to create the arc shape depicted in accompanying drawings which maximizes the surface area for suture needle targeting.

Second Set of (Suture guide or Outer) Rods (200)

Referring again to FIG. 1, a second set of rods 200 are disposed peripheral to the tendon and the first set of rods 100.

In the embodiment shown, the second set of rods 200 include four rods 201-204 (as best shown in FIG. 4) that are spaced from the tendon 10 and span the posterior-anterior plane of the patient. In the embodiment shown, first and second rods 201-202 are configured as two pairs, one pair 201-202 disposed on the lateral side and are aligned about a common (vertical as shown in FIG. 4) axis A-A. Similarly, a second pair (i.e. rods 203-204) are disposed on the medial side and aligned about a common axis in the posterior-anterior plane. In some embodiments, the rods of either pair (i.e. medial or lateral side) of the device can be offset such that a first rod, e.g., rod 201 is positioned at the most medial location while second rod 202 is positioned laterally inward (and closer to the tendon 10). The rods of each pair can be disposed proximate the edges of the rectangular base, and extend parallel to each other over their entire lengths.

In some embodiments, rods 202 and 203 are disposed in the same posterior-anterior plane as the first rods 102, 103; and rods 201 and 204 can be disposed in the same posterior-anterior plane as rods 101 and 104. In some embodiments, rods 101 and 104 are disposed a greater distance in the anterior direction than rods 201 and 204. In some embodiments the relative distance between a rod of the first set of rods (e.g. 102) and a rod of the second set of rods (e.g. 202) can be fixed. Alternatively, this distance can be adjustable in other embodiments.

The second set of rods 201-204 can be discrete members that are each attached to the base 302. The rods 201-204 can be equidistantly spaced from the handle 300, with uniform gaps/space between the rods (i.e. 201-202 and 203-204) of each pair, or positioned in a varied pattern. As shown the rods 200 are spaced from the tendon and do not engage or contact the tendon. In some embodiments, the spacing between rods 200 can be adjusted to provide a range of settings to accommodate suture needles of varying size. For example, the rods 200 can be adjusted by shifting or sliding the rods 200 within tracks formed in the base 302 that lockingly receive the proximal end of the rods 200. Additionally or alternatively, each of the rods 200 can articulate independently of the other rods. Similarly to the adjustment of the first set of inner rods 100 described above, the second set of outer rods 200 can likewise be adjusted via a wheel/gear on the handle do increase/decrease of either, or both, pairs or rods. For example, rods 201 and 202 can be adjusted in the posterior-anterior plane to increase the spacing/gap therebetween to accommodate larger suture needles, and allow for a clamp to be applied, if so desired.

While the first set of rods 100 described above can, in some embodiments, be inserted under the skin and in the paratenon section 12 of the tendon 11, the second set of rods 200 are configured to remain spaced from the tendon and serve as boundaries for suture needles. As disclosed above, as the first set of inner rods 100 and second set of outer rods are can be adjusted relative each other, the physician can position the outer rods 200 as desired (relative to inner rods 100) to ensure that the inner rods 100 are not contacted during insertion of the suture needles 500.

For example, the device can effectively be divided into left/right side (or Lateral/Medial) sets of rods with the left/lateral set of outer rods 201, 202 and inner rods 101 and 102 all moving in unison in a first direction (e.g. laterally); while the rods on the right/medial side set of outer rods 203, 204 and inner rods 103 and 104 all moving in unison in a second direction (e.g. medially). This allows for the physician to open (the two halves diverge laterally and medially relative each other) and close (the two halves converge laterally and medially relative each other) the device which facilitates placement of the device within the paratenon and sliding the (entire) device proximally.

Although the exemplary embodiment shown depicts the second set of rods 200 as including four rods, additional (or fewer) rods can be employed to accommodate a range of patient and/or suture needle sizes. Also, the exemplary embodiment depicts uniformly shaped rods having a fixed length and permanently attached to the base 302, however alternative configurations can be employed including rods of different shapes/sizes/lengths; removable/replaceable rods; and rods of varying length (e.g. telescopingly extendable/retractable). Additionally, all the rods disclosed herein can be integrally formed with the base 302, or formed as separate discrete components that are fixedly attached/coupled to the base.

Figure 7:
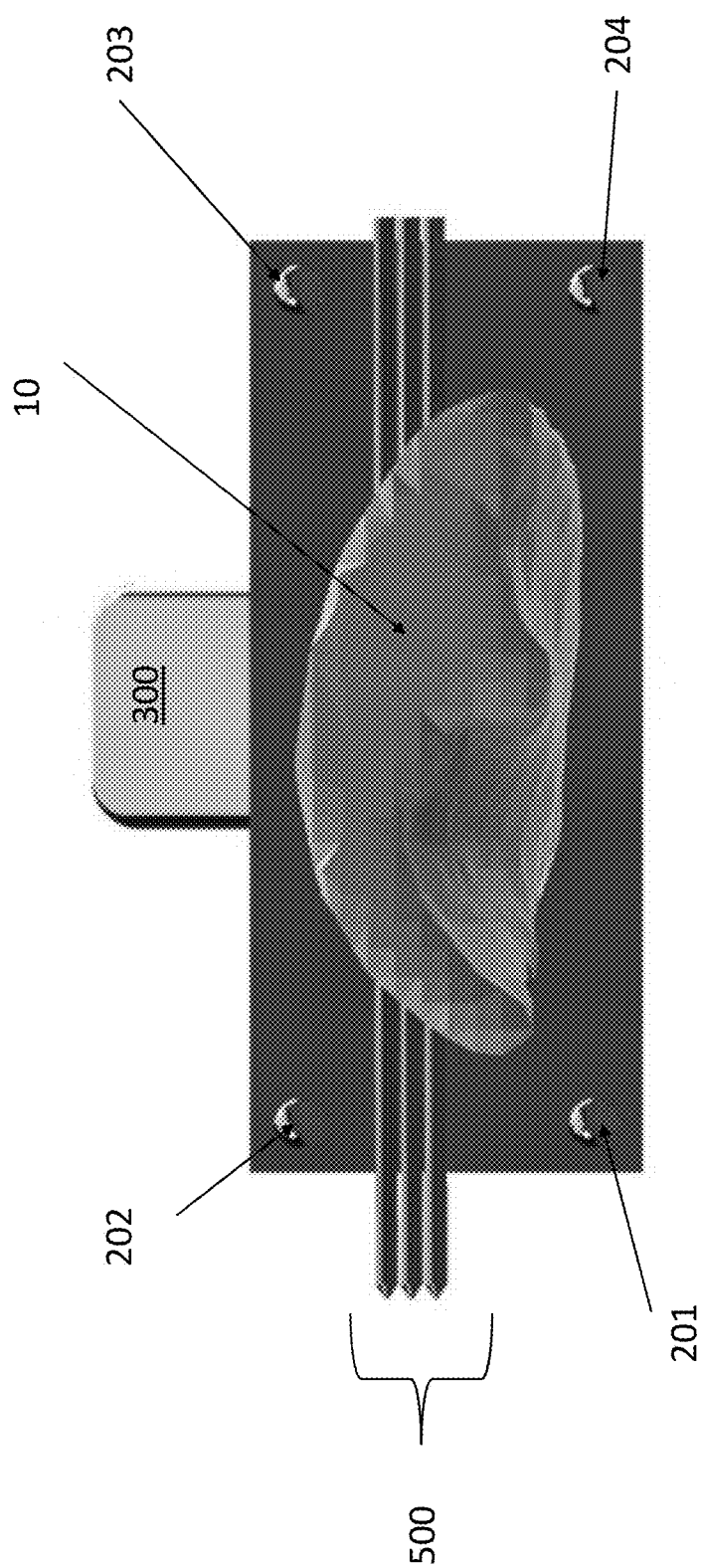
FIG. 7 is a front/axial view of an exemplary embodiment of the Achilles tendon repair device including an exemplary suture guide housing and needles passing though the tendon.
Figure 8:
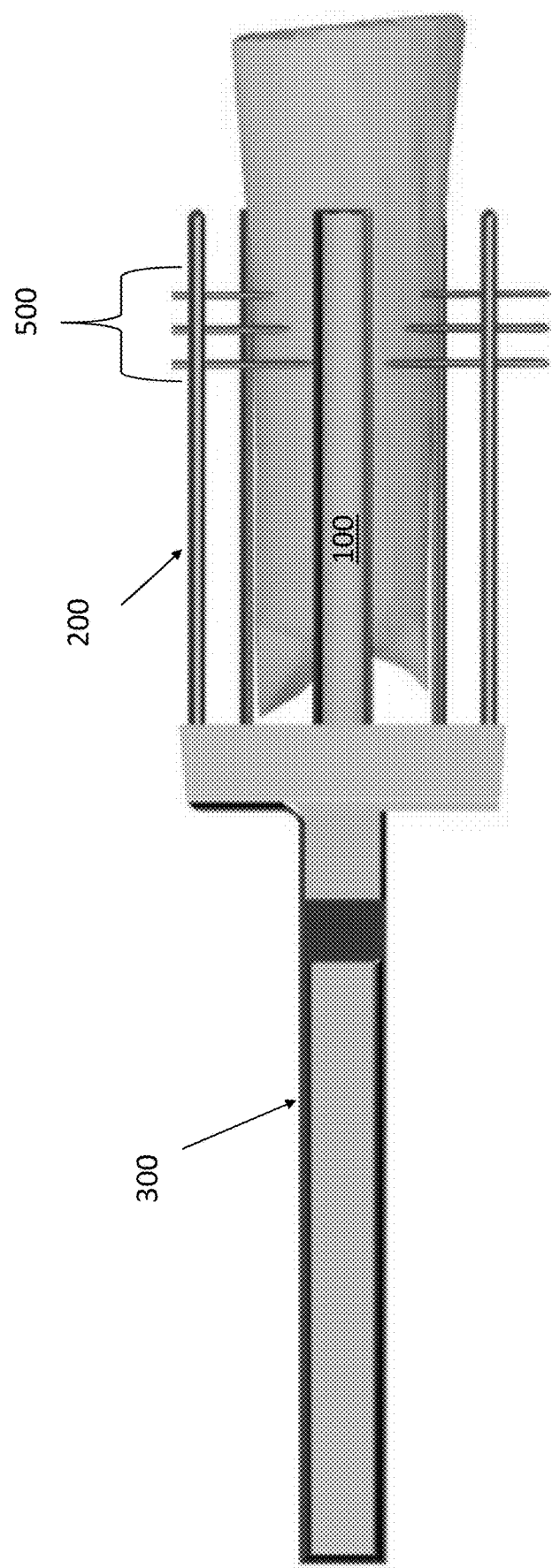
FIG. 8 is a top view of an exemplary embodiment of the Achilles tendon repair device including exemplary suture needles passing though the tendon.
Figure 9:
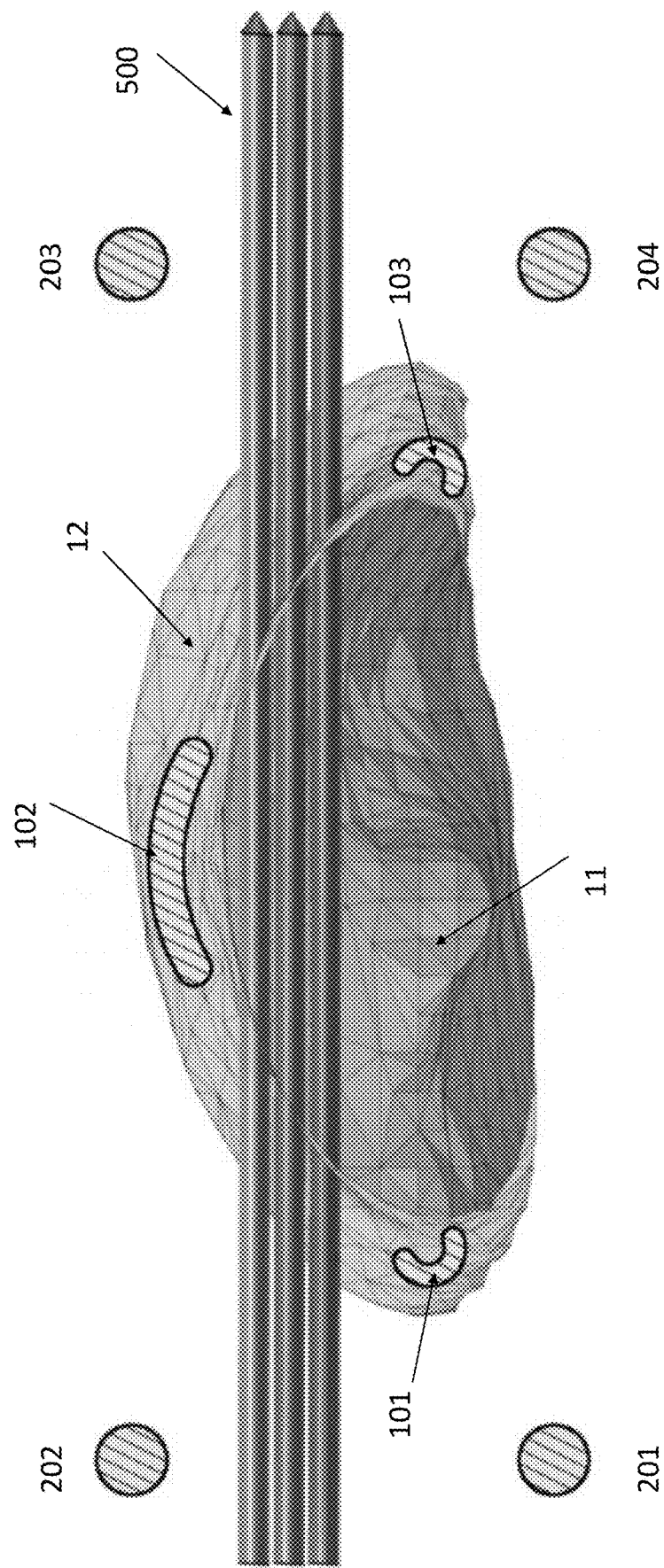
FIG. 9 is cross-sectional view of an exemplary embodiment of the Achilles tendon repair device including exemplary suture needles passing though the tendon, and inner rods of an alternative (arcuate, non-cylindrical) geometry.

In accordance with another aspect of the disclosure, during suturing of the tendon, needles 500 can be inserted between either pair of rods 201-202 and 203-204 over a much wider range of angles than is permitted with conventional suture guides which restrict the physician to predetermined and fixed insertion angles, as shown in FIGS. 7-9. Instead, the present device provides boundary rods 201-204, or guide posts, that allow the physician to move a suture needle anywhere along the entire length of the boundary, and for the needle to pivot or rotate over a range of angles in the posterior-anterior plane. Accordingly, sutures can be inserted as close to each other as the physician deems appropriate, rather than what is permitted via the restricted/dedicated guide paths of conventional devices.

In the exemplary embodiment shown three needles can be inserted between adjacent rods (i.e. between rods 201-202 and between rods 203-204) of each pair of second rods. Additional, or fewer, suture needles can be inserted as desired to provide the requisite amount of suturing for a particular patient. The suture needles 500 can be inserted to pass on the posterior side of (or over, as viewed in FIG. 8) the first set of rods 101, 104 and into the tendon. Additionally or alternatively, the suture needles 500 can be inserted to pass on the anterior side of (or below, as viewed in FIG. 8) the first set of rods 101, 104 and into the tendon.

Suture Guide Housing (600)

Figure 10:
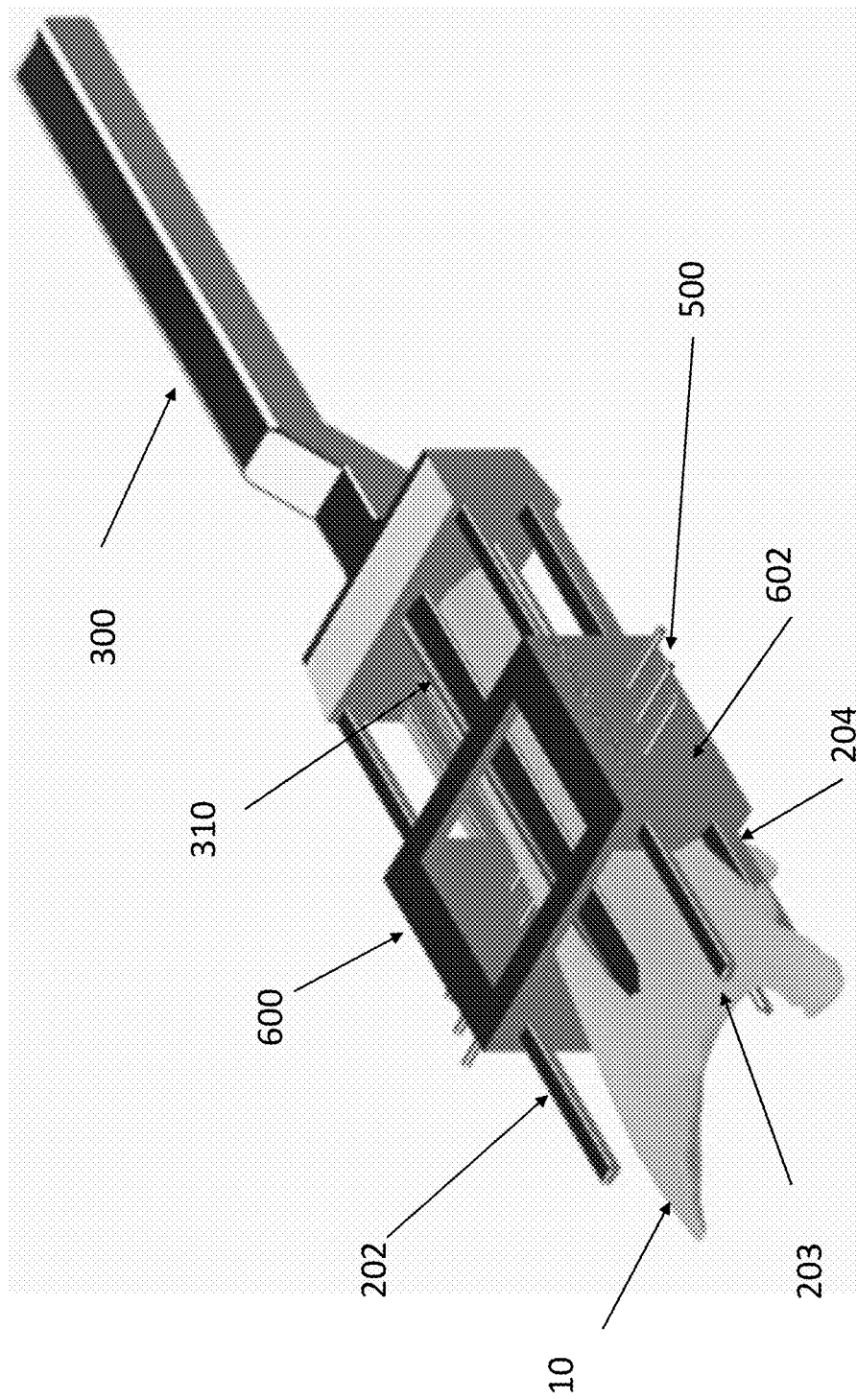
FIG. 10 is a perspective view of an exemplary embodiment of the Achilles tendon repair device including a suture/needle housing to guide insertion of the suture through the tendon.
Figure 11:
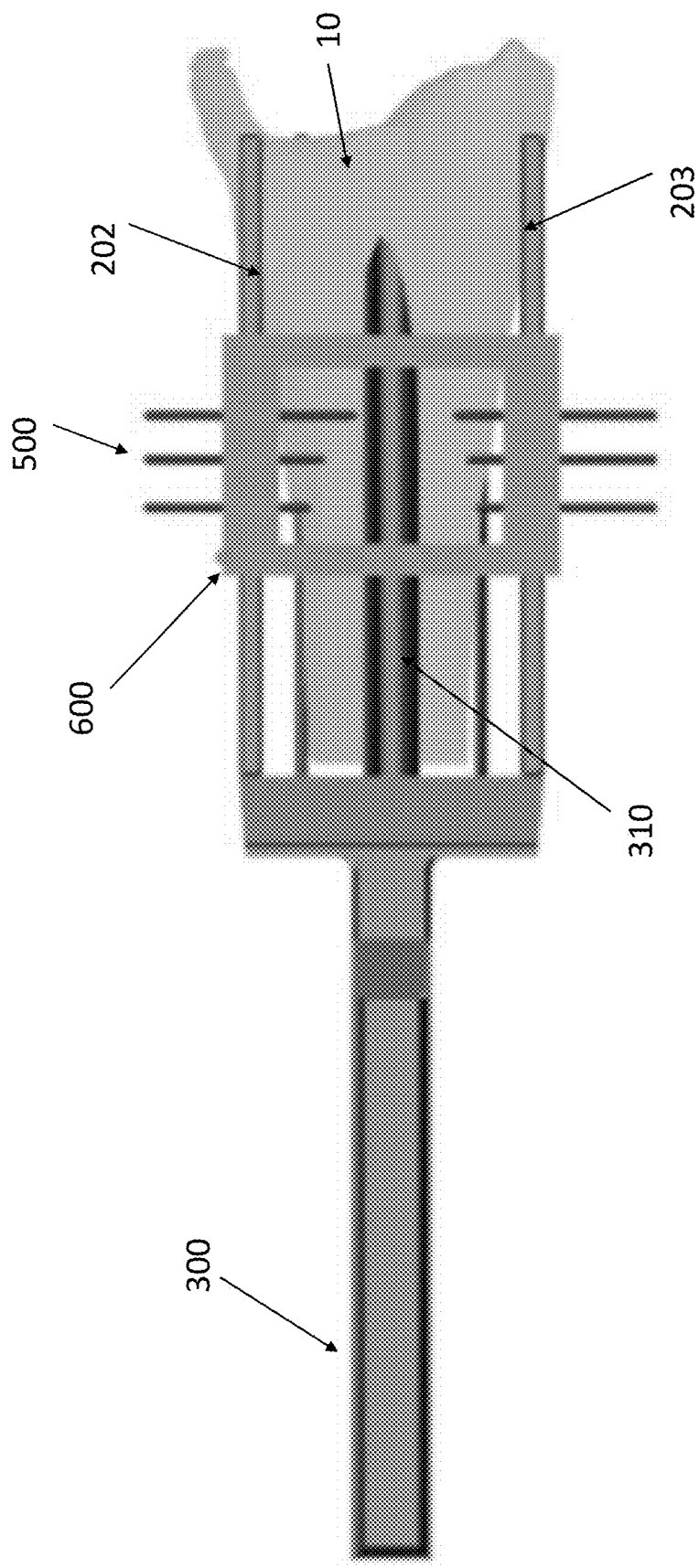
FIG. 11 is a top view of the exemplary embodiment shown in FIG. 10.
Figure 12:
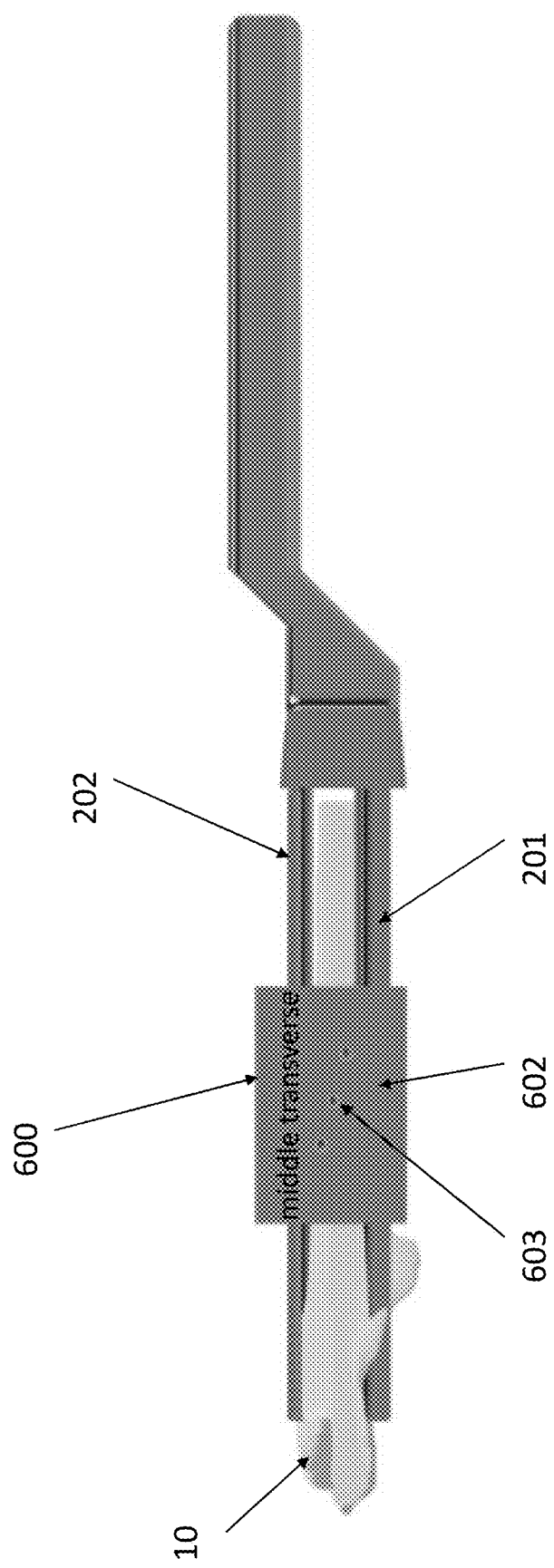
FIG. 12 is a left side view of the exemplary embodiment shown in FIG. 10.
Figure 13:
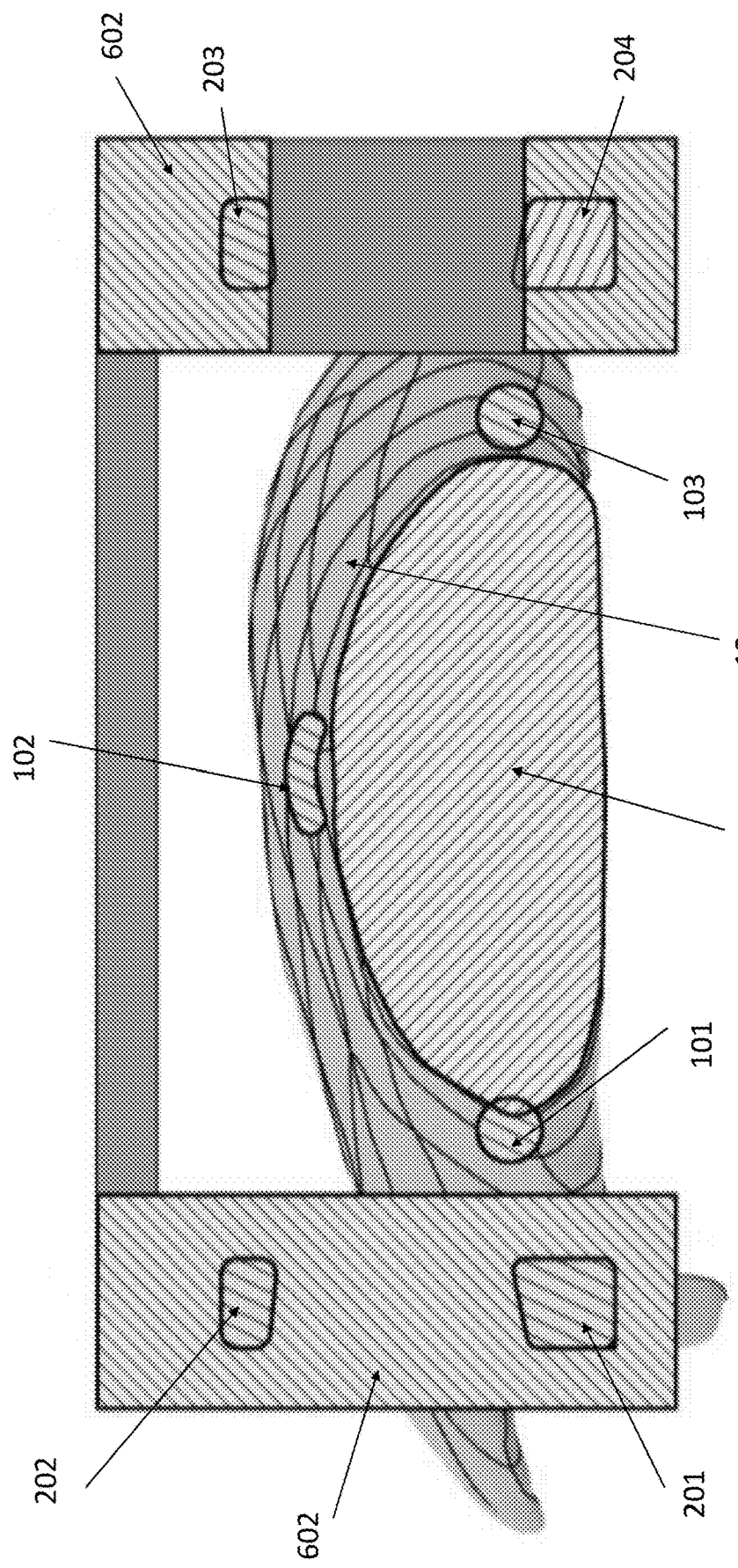
FIG. 13 is a cross sectional view of the exemplary embodiment shown in FIG. 10.
Figure 14:
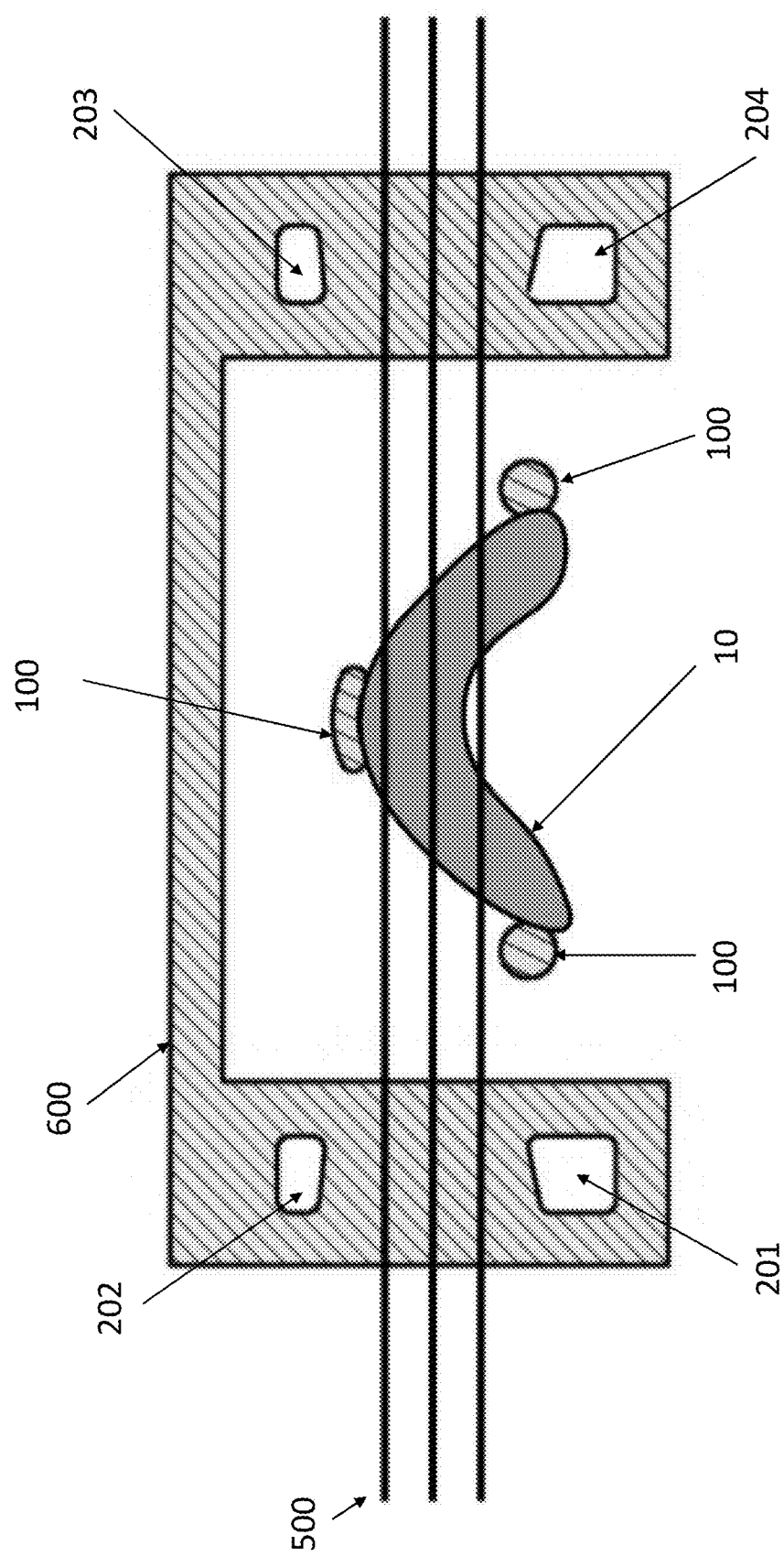
FIG. 14 is a cross-sectional view of the exemplary embodiment shown in FIG. 10 with exemplary suture needles passing through the suture guide housing.
Figure 15:
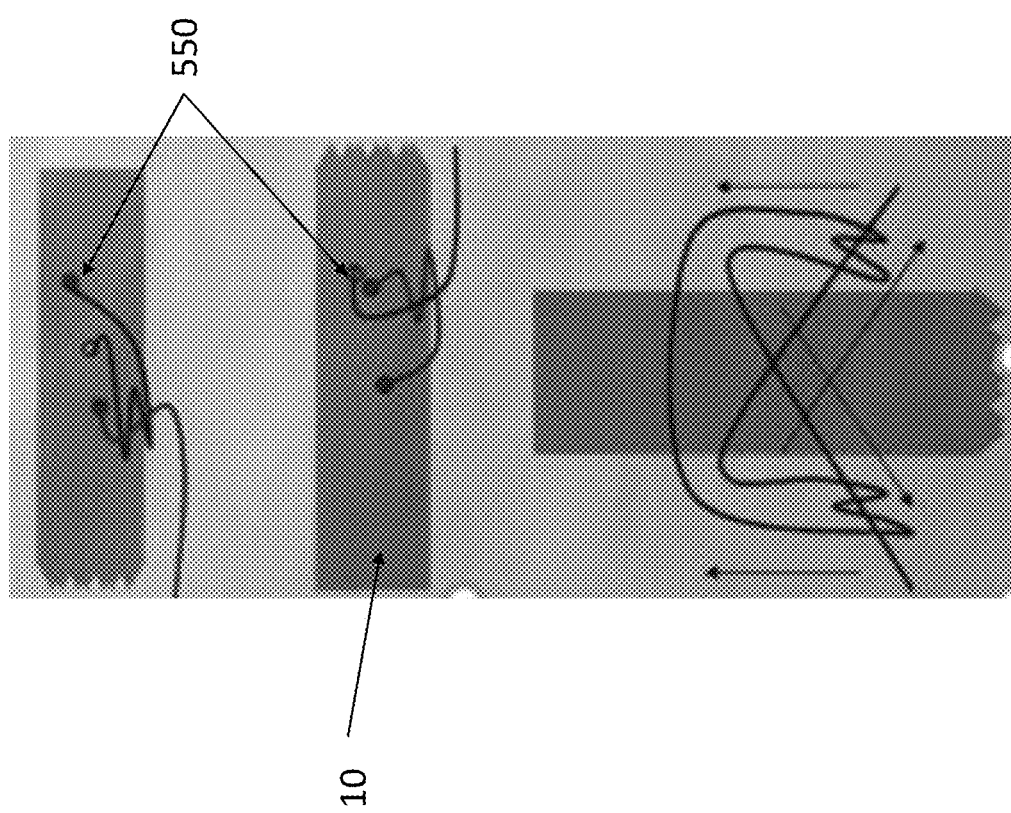
Figure 16:
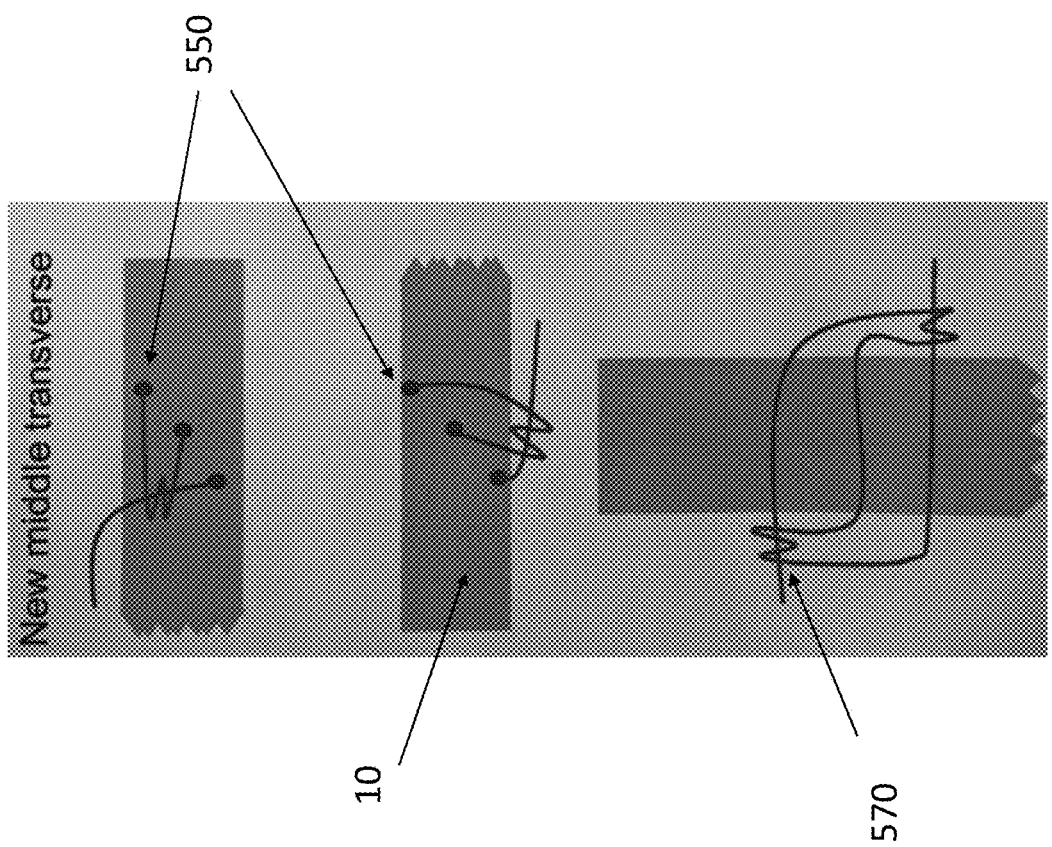
Figure 17:
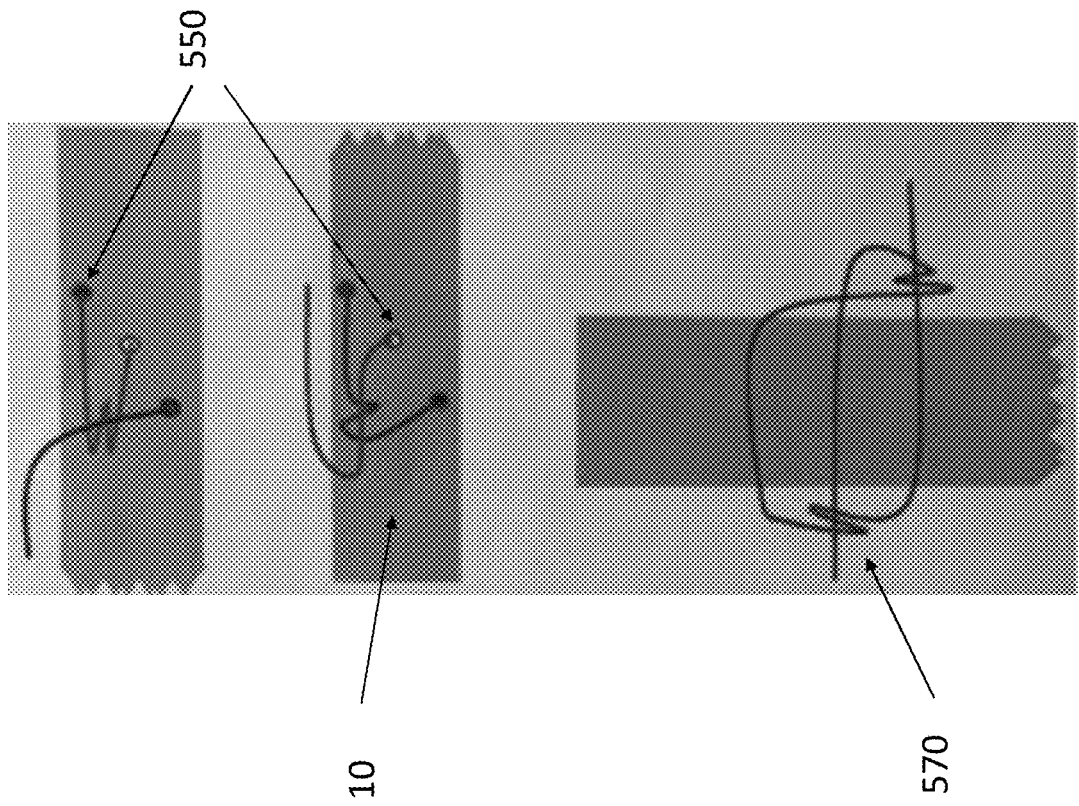
Figure 18:
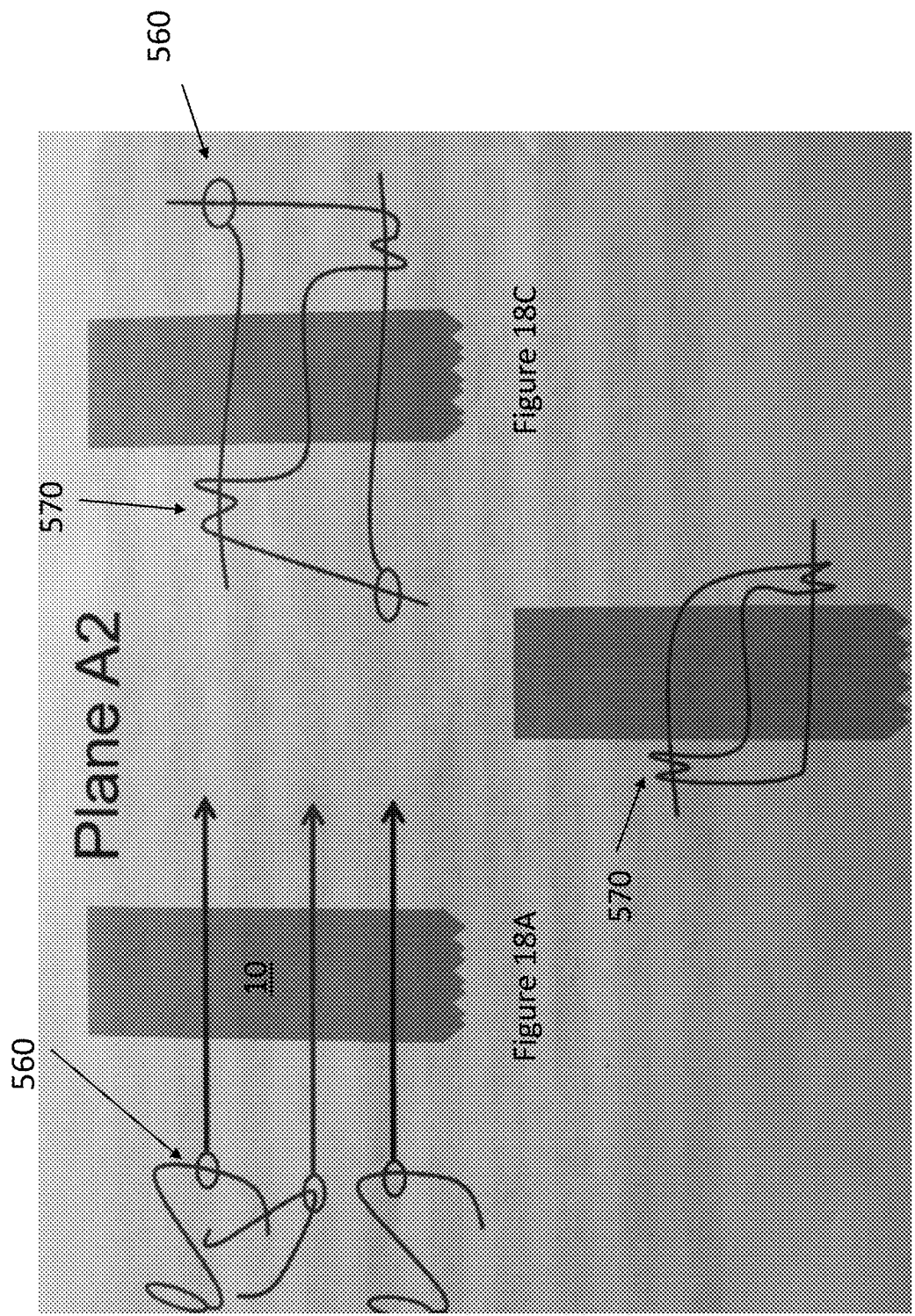

In accordance with another aspect of the disclosure, a suture guide housing 600 can be included, as shown in FIGS. 10-14. In the exemplary embodiment shown, the suture guide housing 600 can be slidingly inserted onto the second rods 200 and includes sidewalls 602 with designated holes 603 for receiving the suture needles 500, with the suture guide 600 remaining outside of the patient's skin. The suture guide housing 600 can be a generally rectangular structure that has a port located at a complimentary position (e.g. at the four corners as shown in FIGS. 10, 13 and 14) to the second set of rods 200 so that each of the rods 201-204 can be inserted into a respective port of the suture housing guide 600. However, alternative shapes/sizes of suture guide housings can be employed and are within the scope of the present disclosure. For instance any suitable geometry (e.g. sidewalls) can be employed which provides dedicated/fixed access points for suture needle insertion.

The holes for guiding the suture needles can be arranged in a predetermined manner—e.g. staggered at different heights along the sidewall 602, and/or spaced about different lengths of the sidewall, as shown in FIG. 12. Although the exemplary embodiment depicts three holes in the sidewall, in a diagonal line, any preferred number, diameter or eccentricity (if not a circular aperture) and positioning of holes can be provided. Also, the suture guide housing can be formed with two sidewalls 602, each having holes to receive the suture needles. Alternatively, the suture guide housing 600 can be formed with holes in only one of the sidewalls 602. In such embodiments, the physician can initiate insertion from the housing side with the holes, pass the suture needle through the tendon, and exit on the other side of the tendon—where the presence of holes in the sidewall to guide/restrict needle path is less critical since the suture has already been deposited in the tendon. Further, in some embodiments, the suture guide housing can include only one sidewall 602, having guide holes formed therein, and the opposing "sidewall" being formed as a window (analogous to the open top or roof shown in FIG. 10) to permit unfettered movement of the needle post insertion into the tendon.

Although the embodiment shown depicts the holes 603 configured for a perpendicular insertion of the suture needle (relative to the guide channel sidewall 602), alternative angles (e.g. acute or oblique—measured relative to the posterior/anterior plane) can be included. The suture guide housing 600 can be advanced/retracted along the second set of rods 200 until reaching the desired location for needle insertion, thereafter the suture guide housing 600 can be releasably locked in place (e.g. via pin inserted though rod 200).

In some embodiments, the rods 200 can include indicia (e.g. graduated depth/distance markings) so that the physician can visually confirm the sutures will be inserted at the appropriate location. Also, the suture guide housing 600 can include a window or opening on the posterior (or top as shown in FIG. 10) surface to allow a physician to see the patient's skin. In the embodiment shown, the handle 300 includes an elongated bar 310 which can extend along the posterior surface of the tendon and overlie the first set of rods 100 inserted under the patient's skin to further target the tendon and prevent undesired movement during suture insertion.

FIG. 13 depicts a cross-sectional view of the tendon prior to insertion of the rods 100 of the repair device of the present disclosure (but with the device aligned and ready for insertion into the paratenon section 12 of the tendon 11). FIG. 14 depicts a cross sectional view of the tendon as manipulated into the draped configuration by the rods 100 of the device disclosed herein.

FIGS. 15-18C depict various suture patterns possible with the device disclosed herein. For example, these figures depict insertion, or exit, locations 550 (with the curved line representing the suture) on the posterior surface which are not possible with traditional repair device which restrict the physician's angle of insertion of the needles to specific fixed angles. Instead, with the present device, the outer guide rods 200, and suture guide housing (if present) allow for virtually any angle of insertion desired by the physician, thereby allowing them to target the most desired locations of the tendon to ensure a more secure suturing and thus improved rehabilitation of the tendon. The arrows shown (e.g. in the bottom view of FIG. 15) depict the pattern of suture insertion and tying. As shown in these exemplary suturing patterns with the presently disclosed device, superior locking of the suture can be achieved via the knots 560 on the medial and lateral sides of the tendon 10. Additionally or alternatively, multiple loops 570 of the suture about a prior suture path can be achieved, as shown.

Clamping Mechanism (700)

In accordance with another aspect of the disclosure, a clamping mechanism can be included for more secure engagement with the tendon. In the exemplary embodiment shown in FIG. 19-24, the clamping mechanism 700 can be coupled to the base 302 of the handle (as shown in FIG. 1). In some embodiments, the coupling is releasable and can be achieved via mechanical fastener (e.g. tongue and groove, clamps, clips, screw fasteners, etc.), or magnetic coupling.

Figure 19:
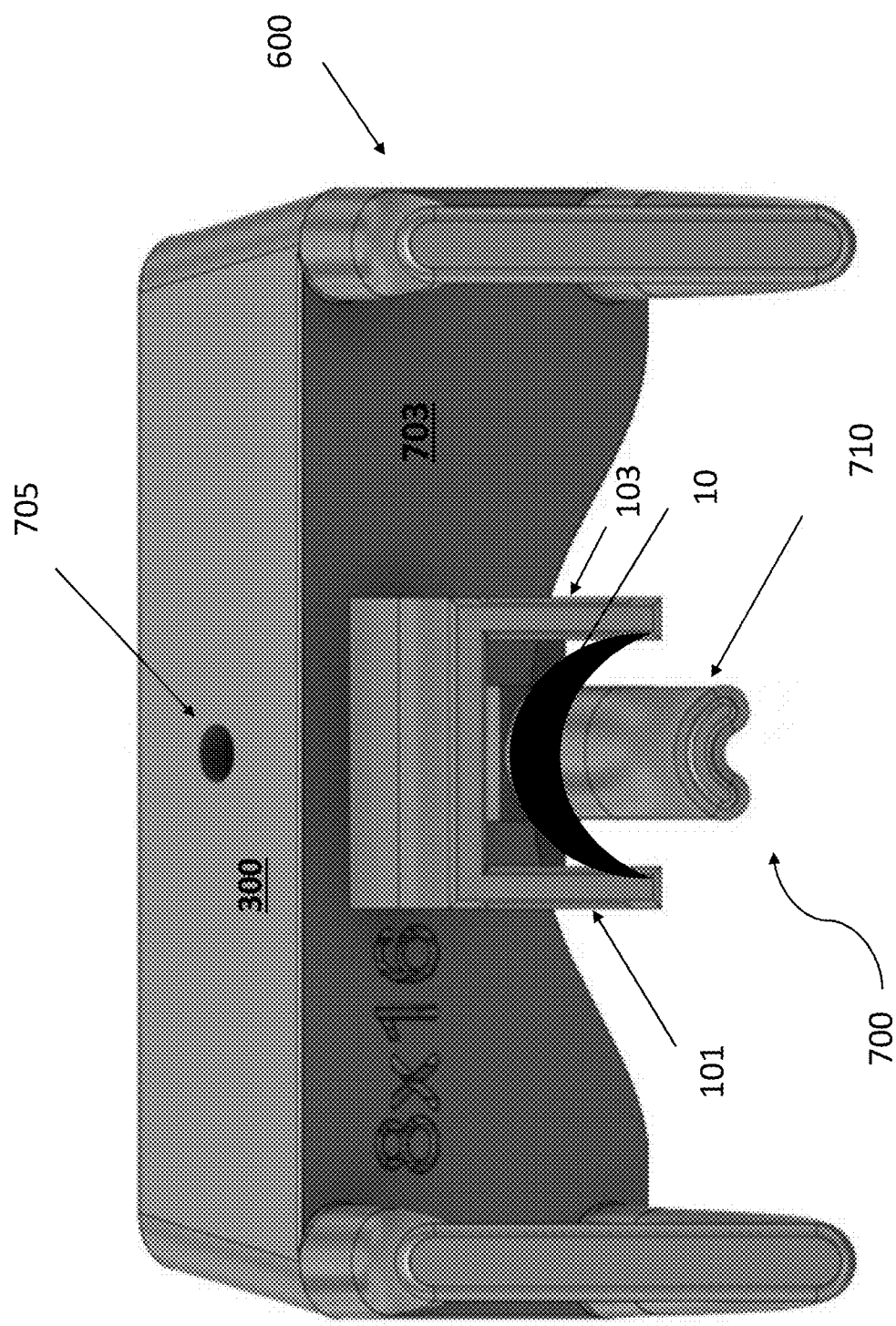
FIGS. 19-23 are depictions of exemplary embodiments of a clamping mechanism for engaging the Achilles tendon (shown in isolation, without the rods of FIGS. 1-14 which impart shape/contour to the tendon for clarity sake) from the anterior side.
Figure 20:
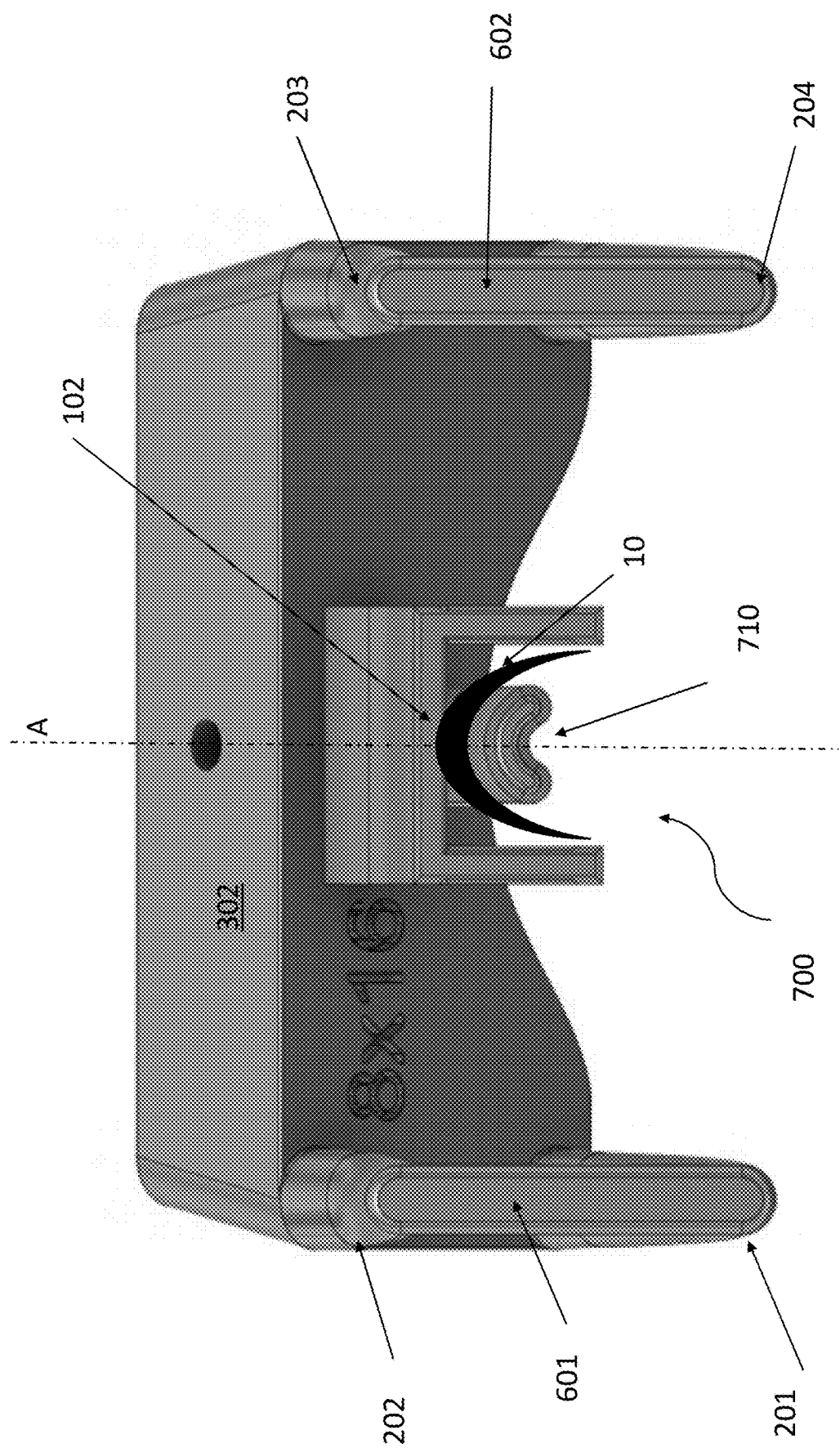

In some embodiments, the clamping mechanism can be combined with the suture housing guide 600, as shown in FIGS. 19-20. The sidewalls 601, 602 of the suture guide housing 600 can extend ("downwardly" as shown in FIGS. 19-20) on both (medial and lateral) sides of the clamp arm 710 (described in further detail below).

A clamp arm 710 is included in the clamping mechanism which can be inserted under the patient's skin, and can articulate over a range of motion in the posterior-anterior plane to engage the tendon. The clamp arm 710 can move in concert with the first set of rods 101-104 described above, provide a clamping force for gripping and retaining the Achilles tendon in the desired position. In the exemplary embodiment shown, the clamp arm 710 is shaped with a non-linear contour (e.g. a convex surface for engaging the tendon, as best shown in FIGS. 19-20, 23-24) which facilitates the anterior-posterior shape imparted to the tendon to increase suture surface area, as described above. The exemplary embodiment depicts the clamp arm 710 having a fixed length and permanently attached to the base 702, however alternative configurations can be employed including clamp arm(s) of different shapes/sizes/lengths; removable/replaceable clamp arm(s); and clamp arm(s) of varying length (e.g. telescopingly extendable/retractable). The distal end of clamp arm 710 can have a tapered tip to facilitate insertion into the patient's skin. The clamp arm 710 can be releasably coupled to the base of the handle 302, e.g., via a threaded fastener which can be received in aperture 705, as shown in FIGS. 19 and 25.

The clamp arm's 710 direct contact with the Achilles tendon on its anterior surface provides sufficient pressure to:
  i. provide confirmation (e.g. visual, tactile and/or haptic) to the physician that the tendon has been properly identified and engaged;
  ii. prevent the tendon from retracting proximally up the patient's leg—which can introduce errors/gaps when inserting sutures;
  iii. manipulate the shape or contour of the tendon by wrapping or bending the tendon in the posterior-anterior plane to increase the surface area available for inserting sutures.

FIG. 19 shows an axial (distal) view of the clamp mechanism with the clamp arm 710 shown in the "down" position, or spaced from the tendon 10 in its furthest anterior position. FIG. 20 shows an axial (distal) view of the clamp mechanism with the clamp arm 710 shown in the "up" position, in its furthest posterior position where it engages the tendon 10 and "pinches" or grasps the tendon in tandem with the inner rods 101-104.

Figure 23:
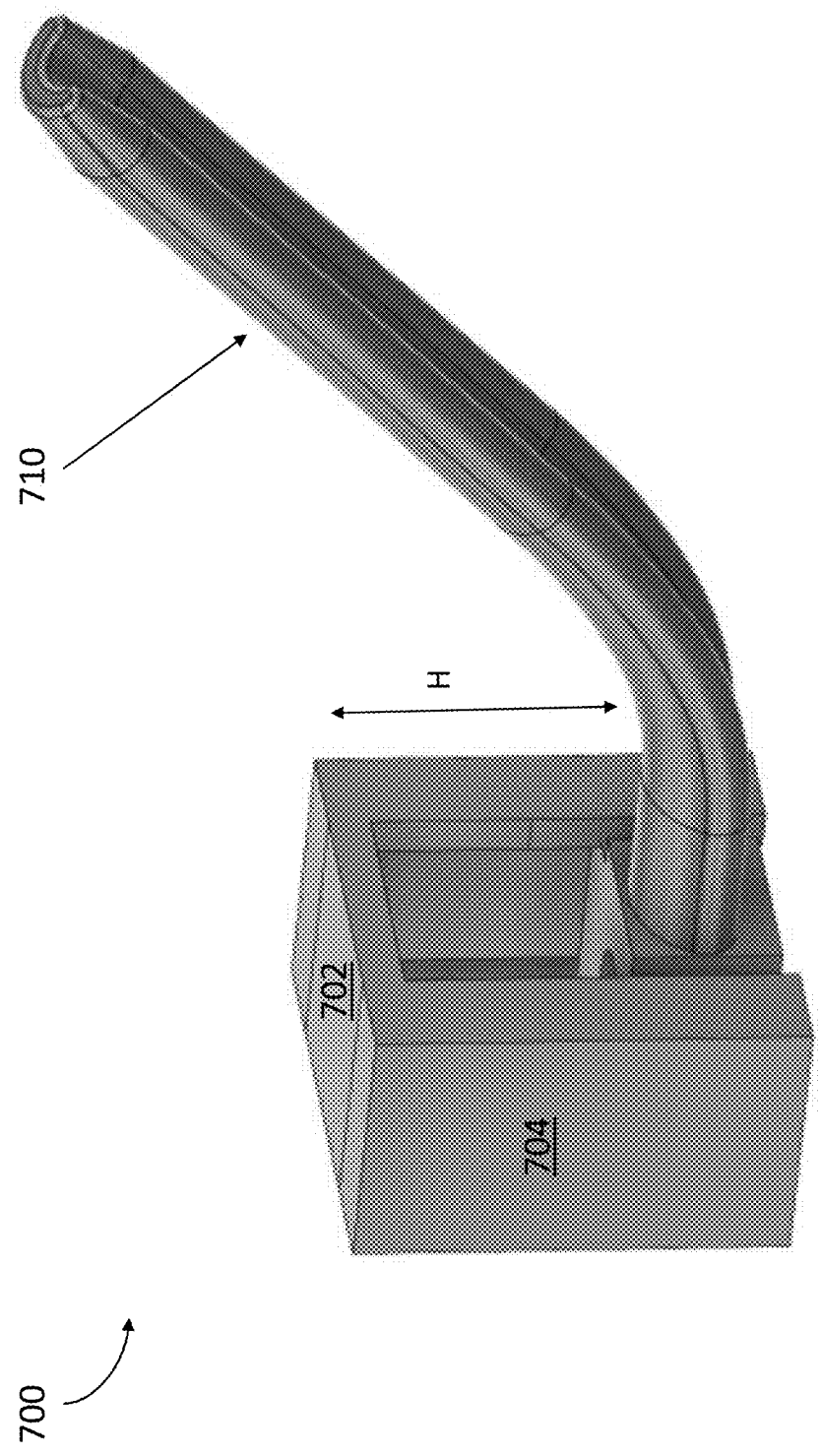

Clamp arm 710 can articulate independently of the other rods 100 and/or 200, and in some embodiments move simultaneously or in concert with (all or select) other rods to converge on the tendon and provide the clamping force. In some embodiments, a wheel or gear can be included in the handle 300 that allows a physician to gradually adjust the relative positioning of the clamp arm 710. For example, rotation of the wheel in a first (e.g. clockwise) direction can gradually bring the clamp arm 710 in closer proximity (in the posterior plane) to engage or grip tendon; while rotation of the wheel in a second direction can gradually displace the clamp arm 710 (in an anterior direction) away from the tendon to release the tendon. Additionally or alternatively, the clamp can have a limited number, or preset, positions (e.g. up and down) in which the clamp arm 710 is triggered for abrupt/rapid movement between positions upon command of the physician. This can be beneficial when the physician has maneuvered the device into a desired location and wishes to quickly capture the tendon before any relative displacement occurs. Additionally or alternatively, in some embodiments, the clamp arm 710 can be adjusted "upward" or "downward" along axis H as shown in FIG. 23 by operation of the fastener coupling the clamp arm 710 to the base 702 of the clamping mechanism, e.g., by rotating the fastener within aperture 705 (shown in FIG. 19) clockwise or counterclockwise.

The clamping mechanism 700 can include side arms 711-714 that extend outward and upward from the first end 710. In some embodiments, these clamp side arms 711-714 can coincide with, and/or be an extension of, the outer/external rods 201-204 described above (e.g., see FIG. 4). In the exemplary embodiment shown in the side views of FIGS. 21-22, the side arm 711, can have a first (larger) radius of curvature than side arm 712 (with side arms 712, 714, obscured due to their location on the opposing side of the device) are formed with complimentary radii of curvature. Thus, the clamping mechanism can be configured as a symmetrical component about its central longitudinal axis "A", as shown in FIG. 20. The clamp arm 710 can be positioned along this central longitudinal axis. In operation, this bent/curved section of the clamping mechanism is where the device exits from under the patient's skin. To improve physician control and accuracy, a window 720 (e.g. opening in the sidewall, if present, between arms 711 and 712; and/or 7134 and 714) can be formed at the radius of curvature so that the physician can view the displacement of the clamp arm 710. In operation, this window 720 coincides with the location in which the device enters the user's skin, thus the opening 720 serves as a window for visual confirmation and monitoring by the physician. The clamp arm 710 can be aligned with overlying rod(s) 101-104 to clamp the tendon therebetween. Additionally or alternatively, select rods (e.g. 102 and 103 of FIG. 4) can be positioned on either side of the underlying clamp arm 710 so that the rods 102, 103 straddle the clamp arm and clamp the tendon in place while also stretching or imparting the desired anterior/posterior shape to the tendon.

Figure 21:
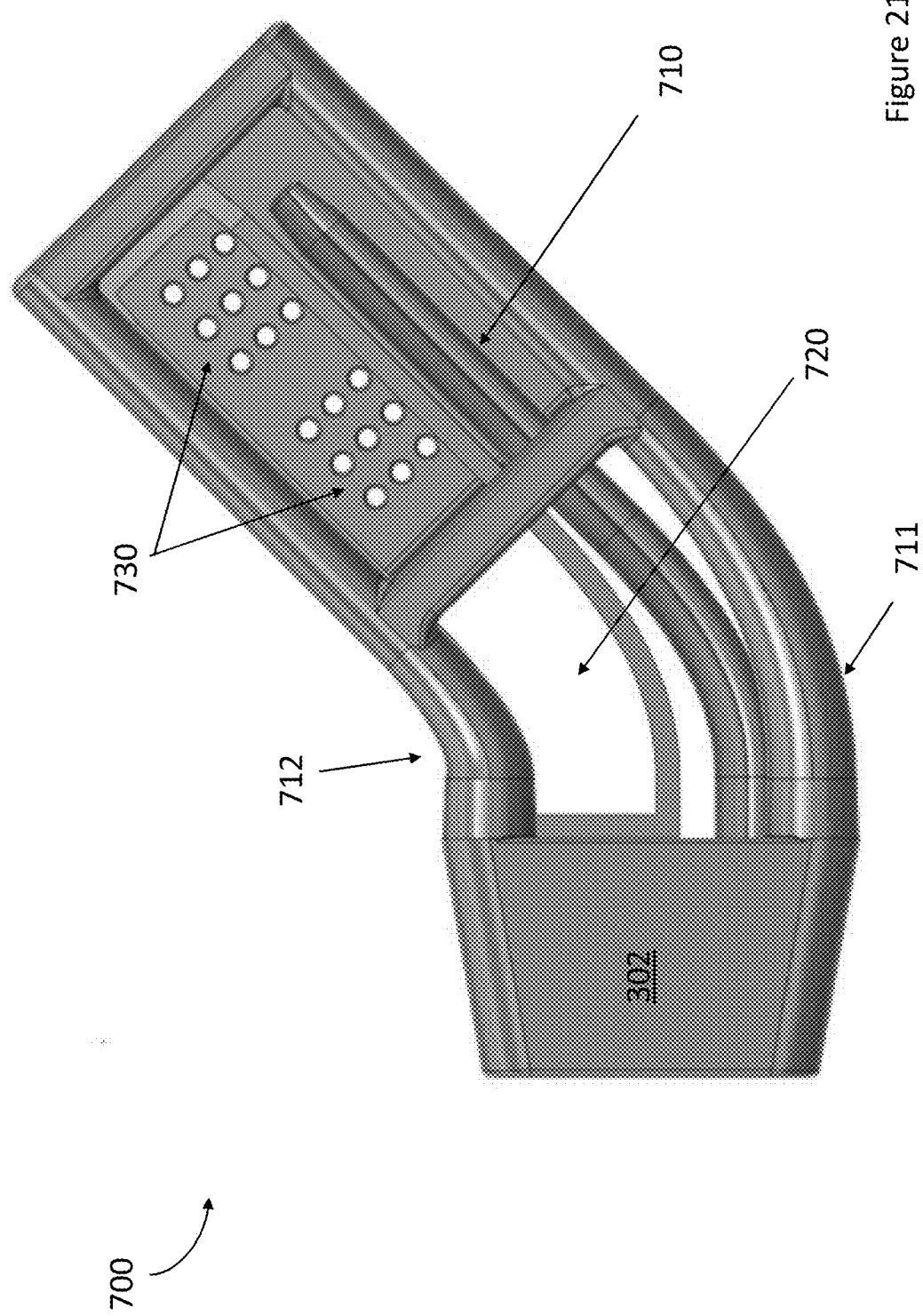
Figure 22:
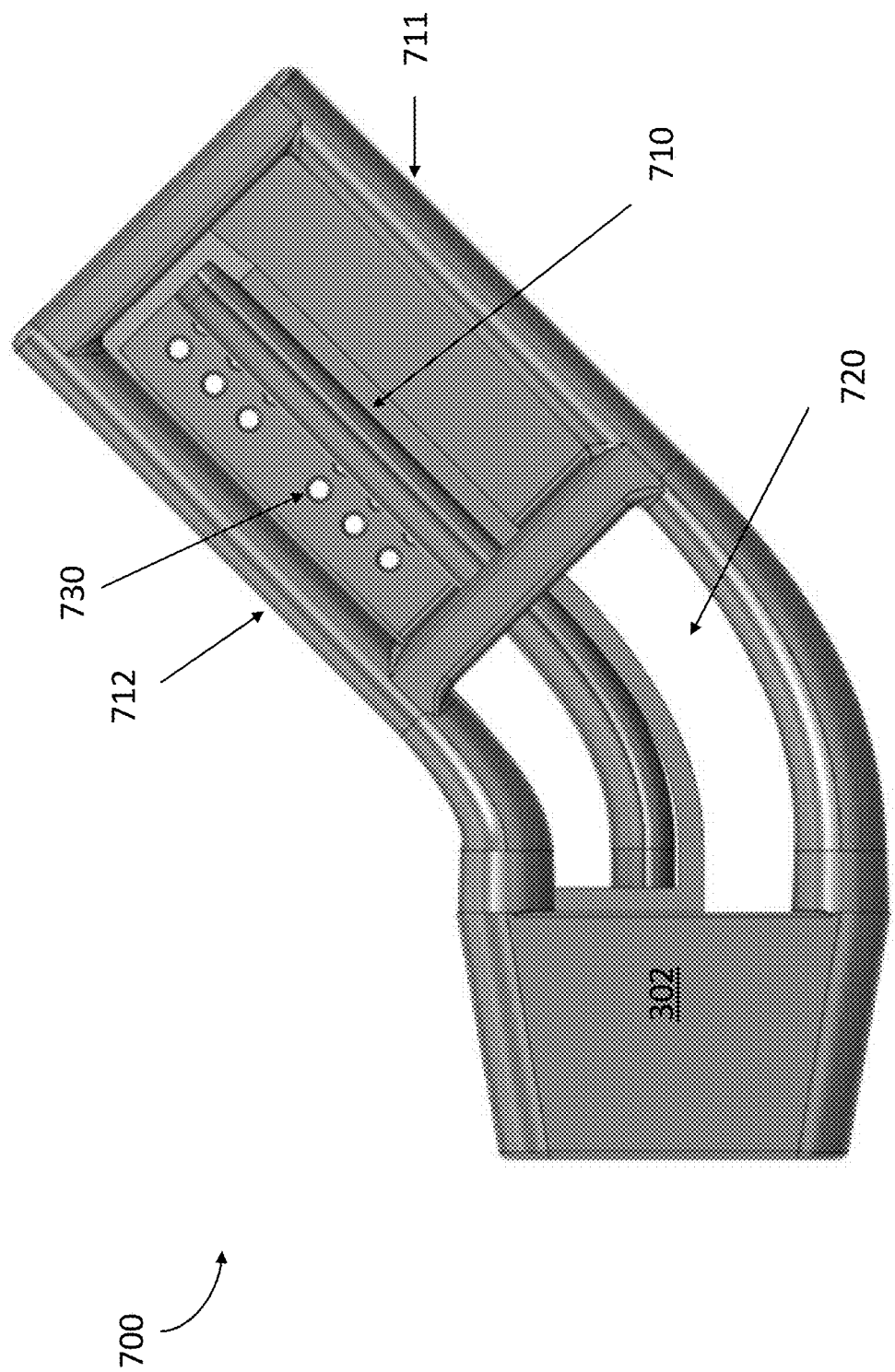

FIG. 21 shows the clamping arm 710 in the "down" position, and FIG. 22 shows the clamping arm as it is displaced in the posterior (relative to the patient) direction into its "up" position where it engages the tendon (not shown for clarity). In the exemplary embodiment shown, the clamping arm is also formed with a radius of curvature such that the distal (relative to the patient) end of the clamping arm 710 is parallel with the arms 711-714. In some embodiments, the radius of curvature of the clamp arm 710 can be adjustable (e.g. arm 710 is flexible via an articulating coil disposed inside the arm 710 that can be bent/extended upon operation of a dial or lever on the handle 310). This allows for the physician to fine tune the radius of curvature to accommodate a variety of patient geometries as well as adjust the clamping force exerted on the tendon. Additionally or alternatively, the radius of curvature of the clamp arm 710 can be fixed, with the entire arm displaced along axis "H" (vertically as shown in FIG. 23, or in the anterior/posterior plane with respect to the patient) along the sidewall 704).

In some embodiments the clamping arm 710 operates in unison with the internal rods 101-104, with the clamping arm 710 moving "up" in the posterior direction while rod(s) 101-104 move "down" in the anterior direction. Additionally or alternatively, the clamp arm 710 can move independently of the internal rods 101-104 to engage, or disengage, the tendon as desired by the physician, thus allowing for resizing and reorienting during the medical procedure to find the desired "fit" and/or grip of the tendon.

Additionally, needles can be inserted between adjacent arms (i.e. between rods 711-712). In some embodiments, the suture guide 600 (as shown in FIG. 10) can slide along rods 711-712 (which, as noted above can coincide with, or be an extension of outer rods 201-204) and provide designated suture paths. In the exemplary embodiment shown in FIGS. 21-22, a sidewall is formed (spaced from the window 720 and at the distal end of the arms) with a plurality of sets of needle holes 730 (e.g. two 3×3 matrices) can be provided which allow for suturing at an angle perpendicular to the sidewall; additionally or alternatively, the suturing can be inserted at an acute or oblique angle as well. Additional, or fewer, suture holes can formed in the sidewalls to provide the requisite amount of suturing for a particular patient. Likewise, alternative shapes/sizes of apertures can be employed and are within the scope of the present disclosure.

The holes for guiding the suture needles can be arranged in a predetermined manner—e.g. staggered at different heights along the sidewall 602, and/or spaced about different lengths of the sidewall, as shown in FIG. 12. Although the exemplary embodiment depicts three holes in the sidewall, in a diagonal line, any preferred number, diameter or eccentricity (if not a circular aperture) and positioning of holes can be provided. Also, the suture guide housing can be formed with two sidewalls 602, each having holes to receive the suture needles. If desired, the clamping mechanism 700 suture sidewalls can be formed with holes 730 in only one of the sidewalls, with the opposing "sidewall" being formed as a window to permit unfettered movement of the needle post insertion into the tendon.

Figure 24:
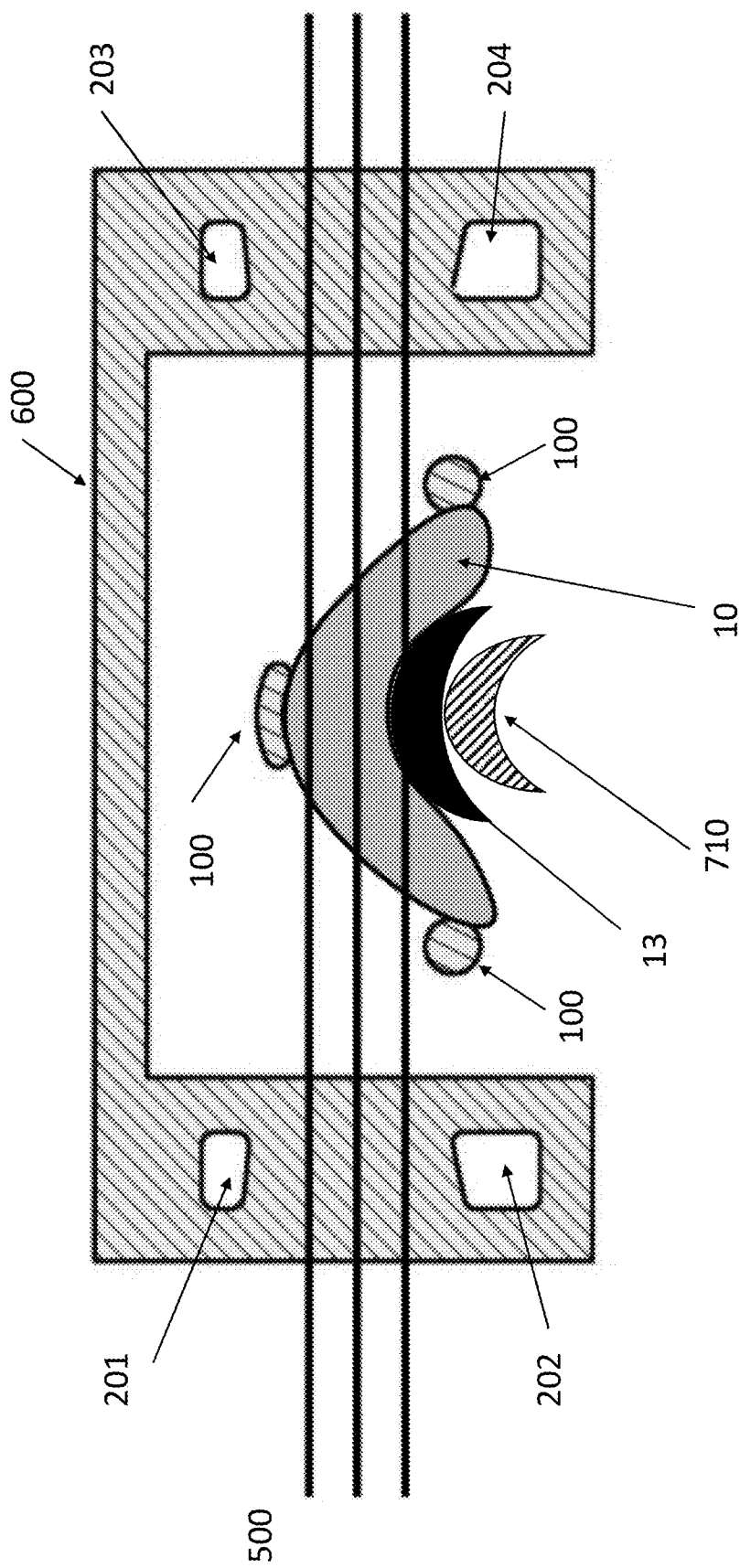
FIG. 24 is a cross-sectional view of an exemplary embodiment of the device including a clamping mechanism, inner rods, outer rods, and suture housing guide which in combination clamp and shaping a portion of an Achilles tendon.
Figure 25:
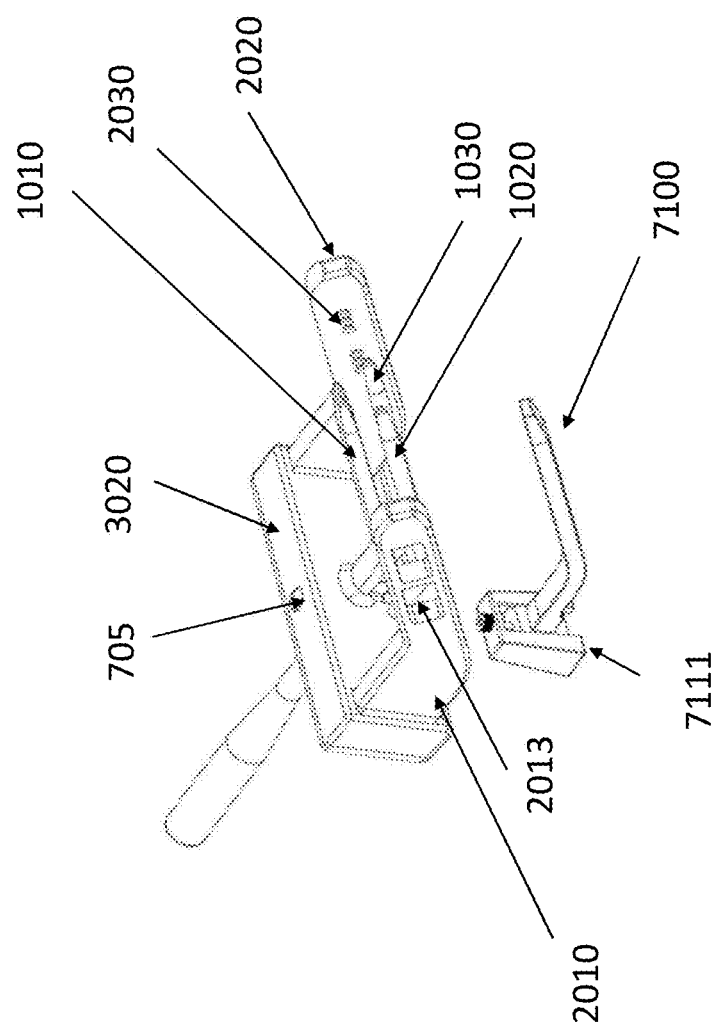
FIGS. 25-34 are additional views of the Achilles tendon repair device, including the clamping mechanism (depicting the rods and clamping member in exploded view).

FIG. 24 illustrates the clamping arm 710, inner rods 100 (only three illustrated in this exemplary embodiment but alternative numbers of rods can be employed), outer rods 201-204, and suture housing guide 600. As shown, the clamp arm 710 and inner rods 100 move relative to each other to clamp/grip the tendon 10. In some embodiments, the clamp arm 710 moves upward wile inner rods 100 remain fixed; in some embodiments the inner rods move down while the clamp arm remains fixed; in some embodiments both inner rods 100 and clamp arm 710 move simultaneously in a converging manner towards each other. This relative movement clamps/grips a portion of an Achilles tendon, and imparts an arcuate shape in the anterior-posterior plane to increase surface area for suturing. FIG. 24 also shows a cross-section of a muscle fiber(s) 13 which can exist "under" (posterior with respect to the patient) at the proximal end of the tendon. The clamp arm 710 can engage the muscle fiber layer 13 (if present) and exert a ("upward" in the anterior direction with respect to the patient) force to drape or bend the tendon (and muscle if present) into an arcuate shape. Similarly to the discussion regarding FIG. 14, sutures 500 shown in FIG. 24 can pass through the guide 600 to repair the tendon.

Figure 26:
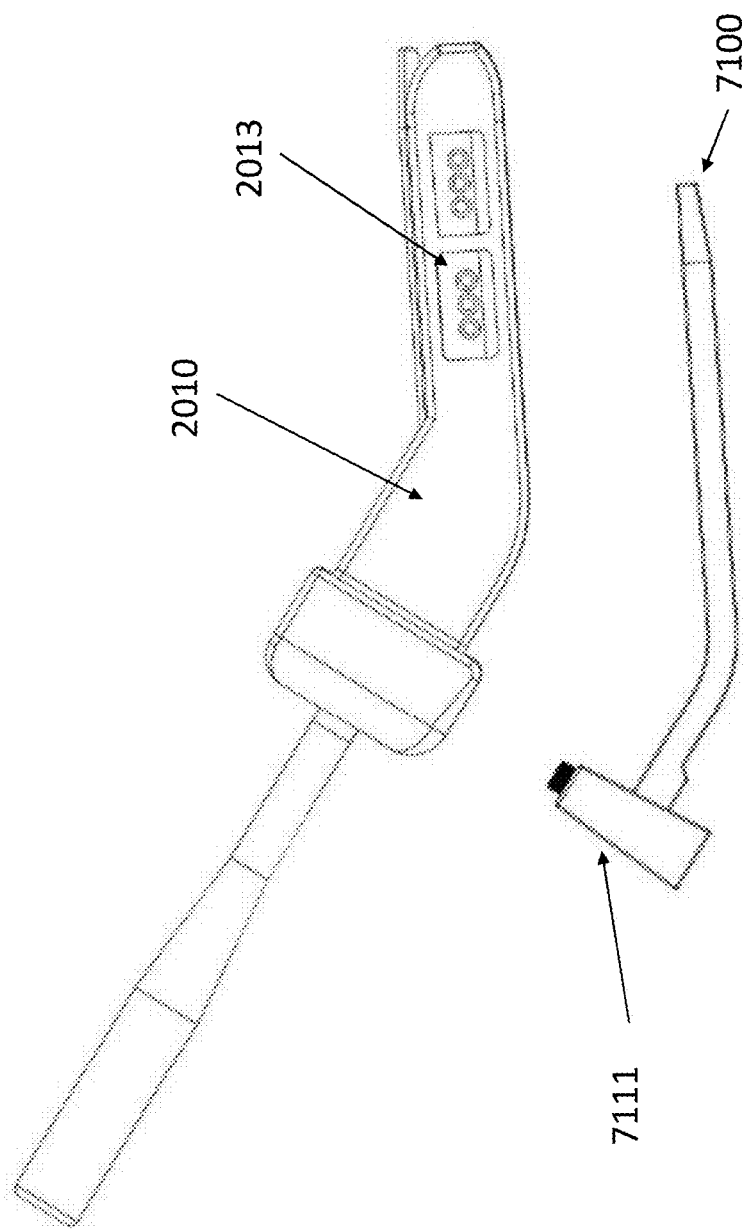

FIG. 25 illustrates an exploded view of the clamping arm 7100, inner rods 1010, 1020, 1030 (only three illustrated in this exemplary embodiment in a triangular/pyramid configuration with inner rod 1010 having an arcuate/saddle shape (akin to a shoe horn), but alternative numbers of rods can be employed). Two outer rods 2010-2020 are included having an elongated/rectangular wall geometry, with apertures or viewing windows 2013 on the left outer rod 2010 and suture guides 2030 on the right outer rod 2020. The clamping arm 7100 can be removably coupled to the handle 3020 via the fastener at the top of the clamping arm mount 7111, as shown in FIG. 26. Additionally, the suture guide housing 2013, 2030 can be configured as a sheath that is attached (e.g. slid over) the outer rods 200. In other words, the rods 200 are positioned underneath the sidewalls of the suture guide housing which define the openings 2013, 2030, as shown. This allows for a variety of suture guide housing designs (e.g. of varying aperture size, location, angle of orientation including perpendicular, acute, obtuse, etc.) to be "swapped out" or interchangeably inserted onto the underlying outer rods 200.

Figure 27:
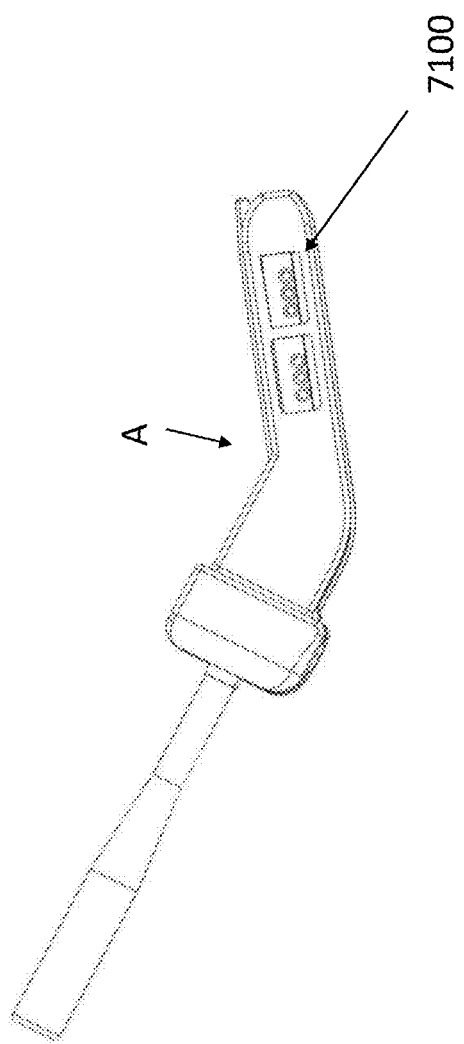

As shown in FIG. 25, the radius of curvature of the claims arm 7100 matches the radius of curvature of the inner rods 1010-1030 (only three shown in this exemplary embodiment), outer rods 2010-2020 (the underlying rods 201-204 are obscured from view here since the suture guide housing is disposed thereon), and suture housing 2013, 2030 (if present). This radius of curvature provides a bend or angle that allows the device to be inserted under the patient's skin, and articulated for operation by the physician, without hitting the patient's heel bone. In some embodiments, this angle is fixed; in others, the angle "A" (as shown in FIG. 27) is adjustable. In the exemplary embodiments shown, the angle is approximately 20° to 60° relative to the longitudinal axis of the handle.

Figure 28:
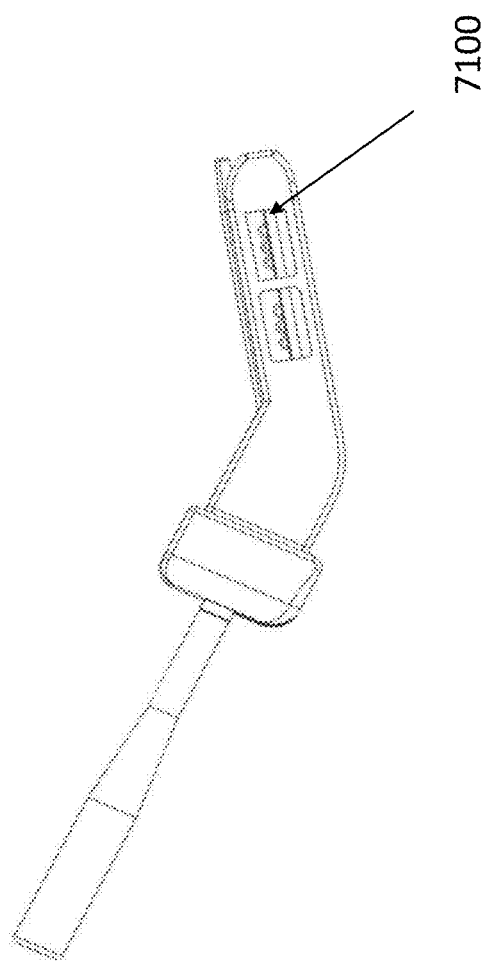

FIGS. 26-28 depict the movement of the clamping arm 7100, as viewed through window 2013 of the left outer rod 2010, with FIG. 26 showing the clamping arm 7100 prior to coupling to the handle, FIG. 27 showing the clamping arm 7100 coupled to the handle and in the lower position (not engaged with the tendon), to FIG. 28 where clamping arm 7100 has been raised (i.e. advanced in the posterior direction), as can be detected by the presence of the arm 7100 within window 2013 and blocking the view of the suture holes 2030 in the distant outer rod 2020.

Figure 29:
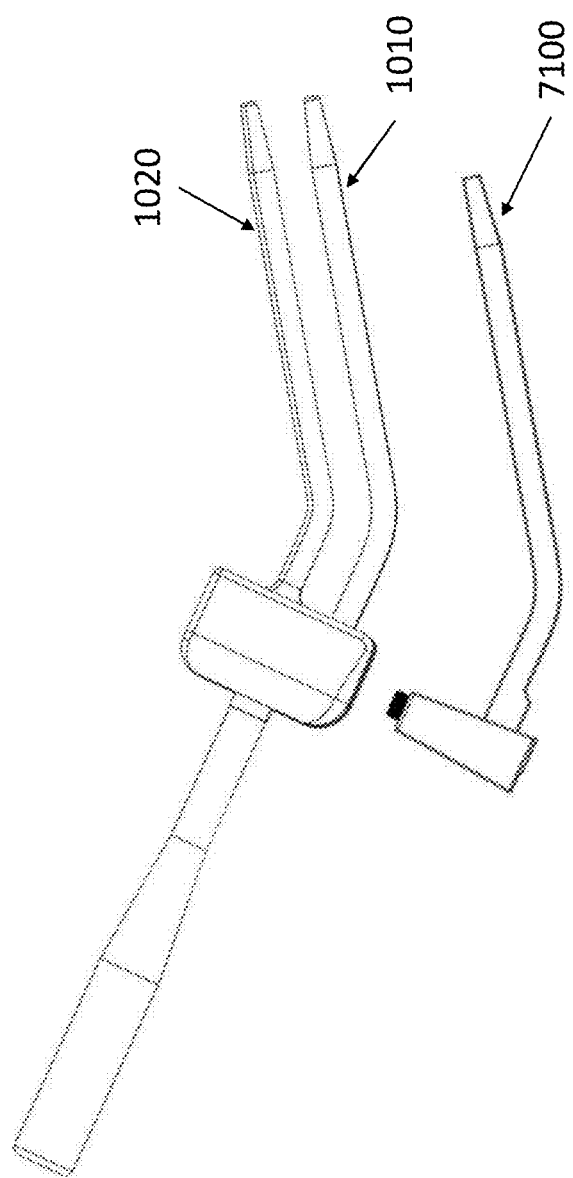
Figure 30:
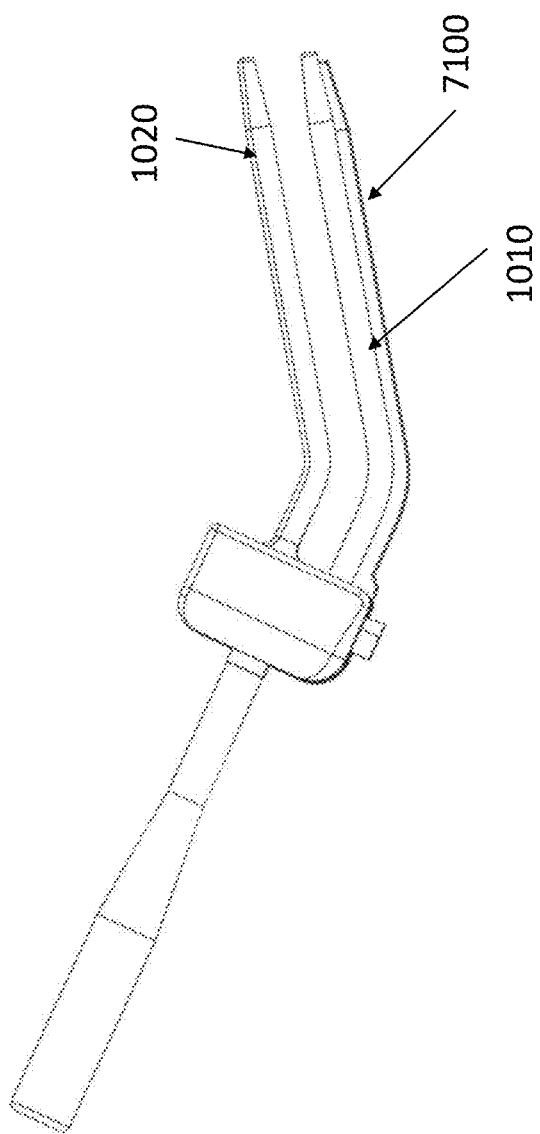
Figure 31:
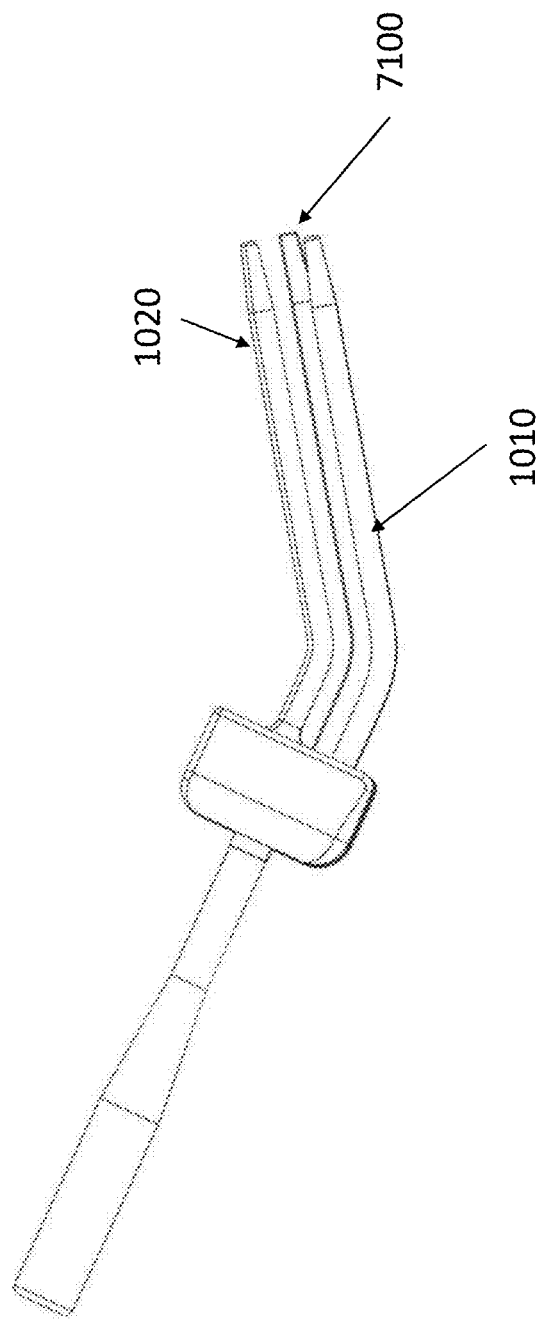

FIGS. 29-31 depict similar views of the progression of the clamping arm 7100 movement in the posterior direction along with the internal rods 1010, 1020. In this embodiment, only internal rods are employed (the outer rods 2010 and 2020, and suture housing are eliminated). For sake of clarity, it should be understood that both sets of internal and external rods can be employed with the clamping arm in some embodiments; additionally or alternatively, the suture housing can also be incorporated in some embodiments.

Figure 32:
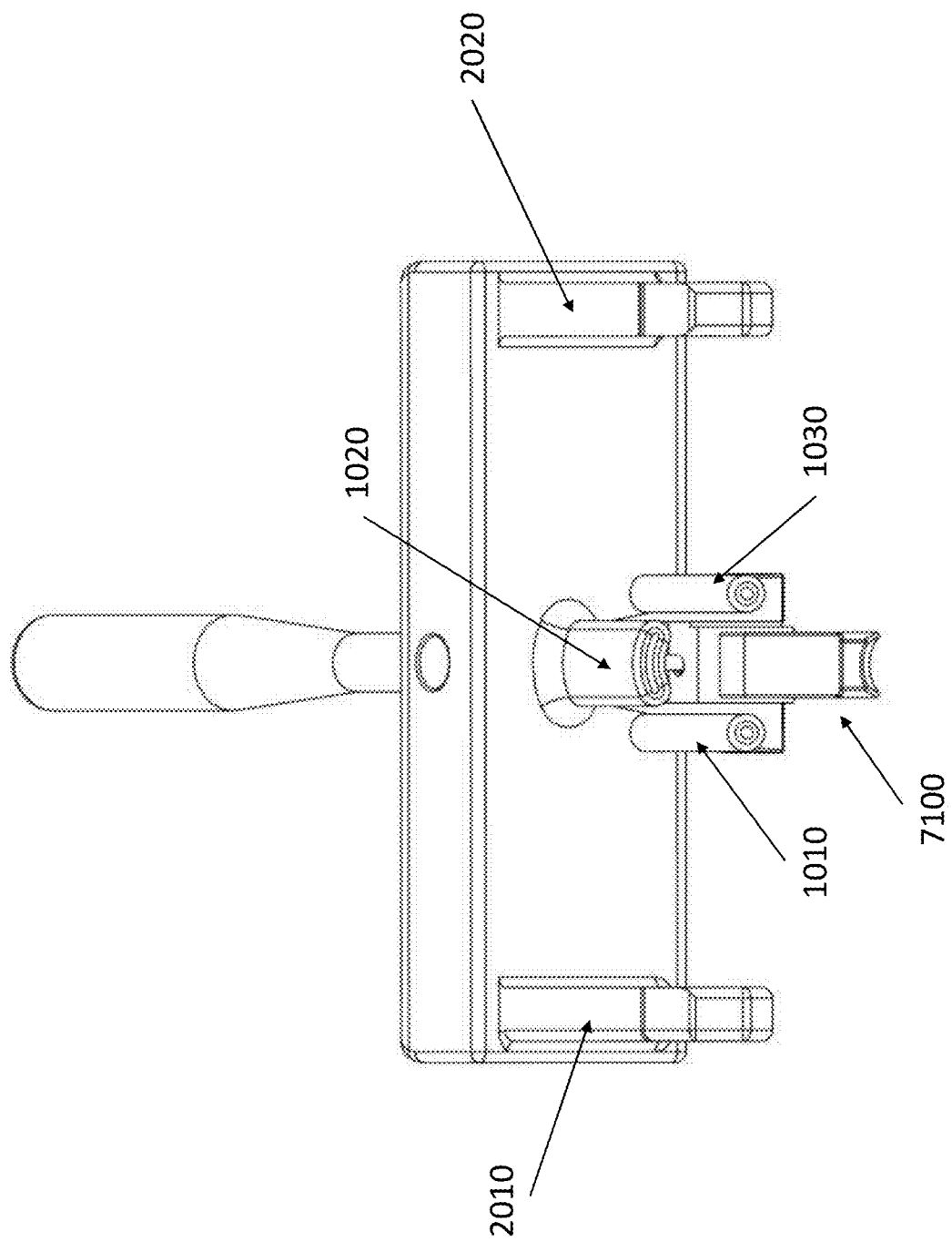
Figure 33:
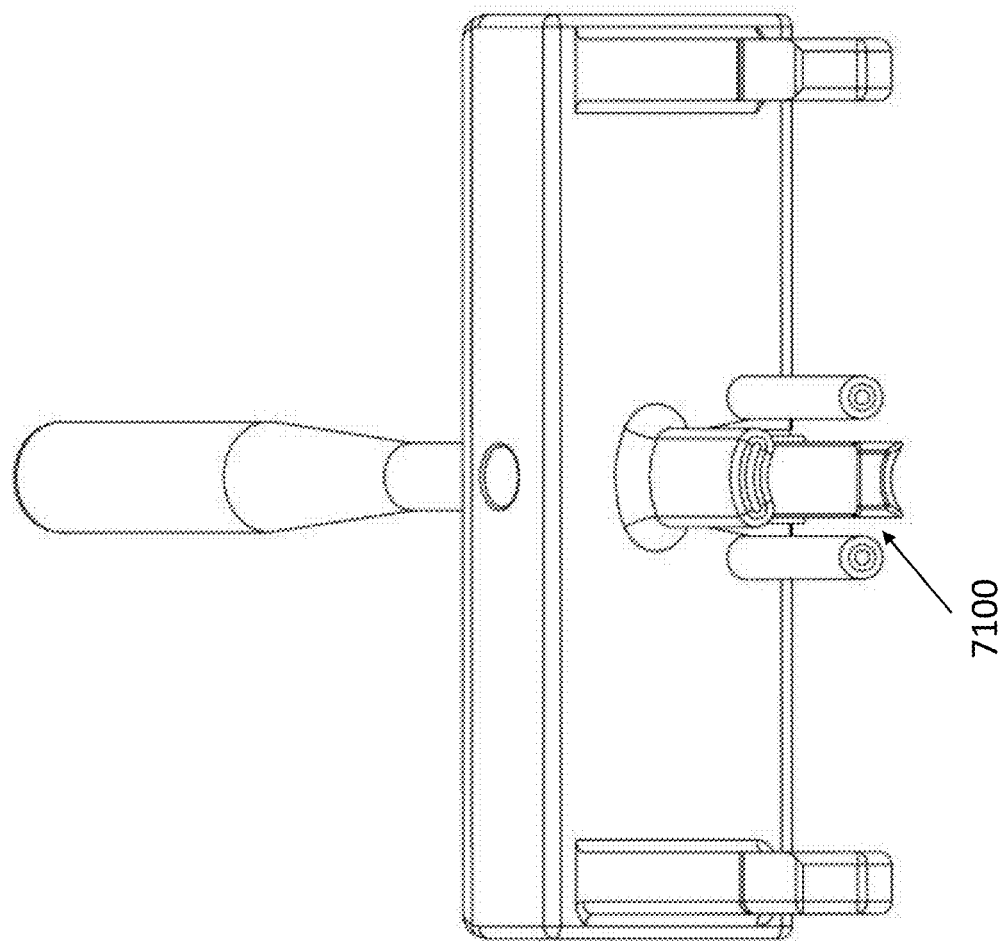
Figure 34:
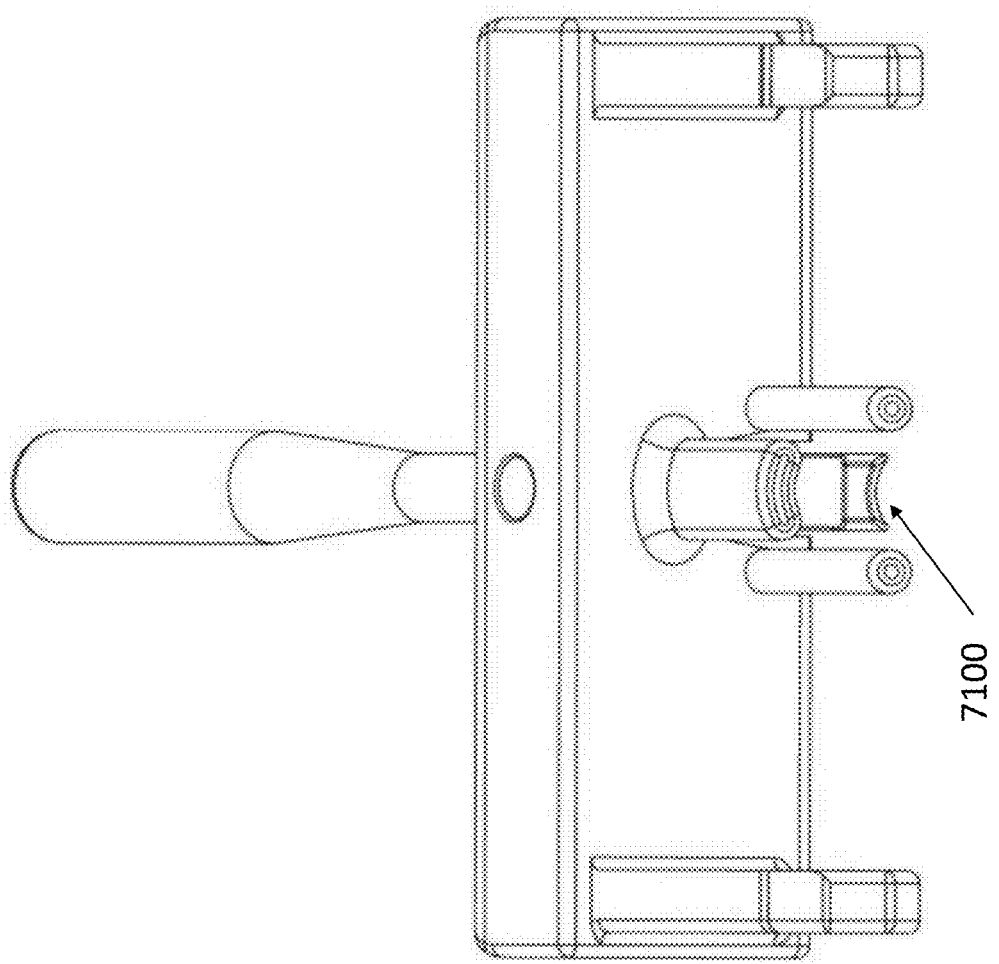
Figure 35:
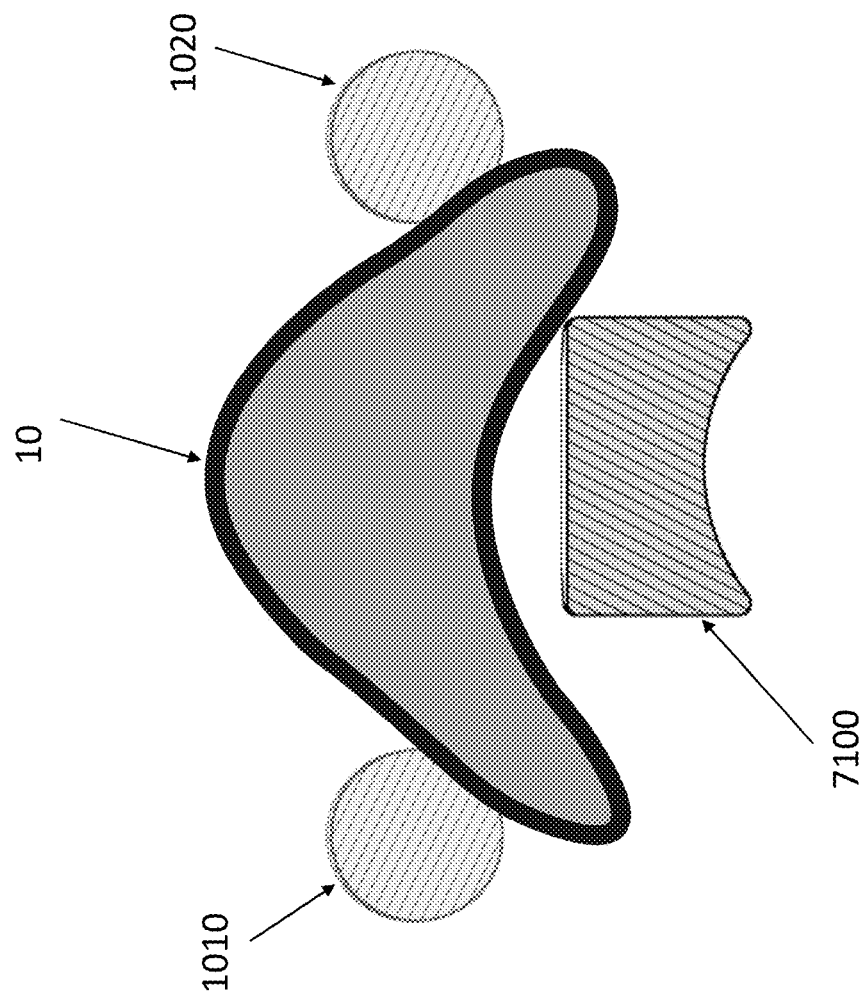
FIGS. 35-36 are cross-sectional views of an exemplary embodiment of the device including a clamping mechanism and inner rods, which can in combination clamp and shape a portion of an Achilles tendon.
Figure 36:
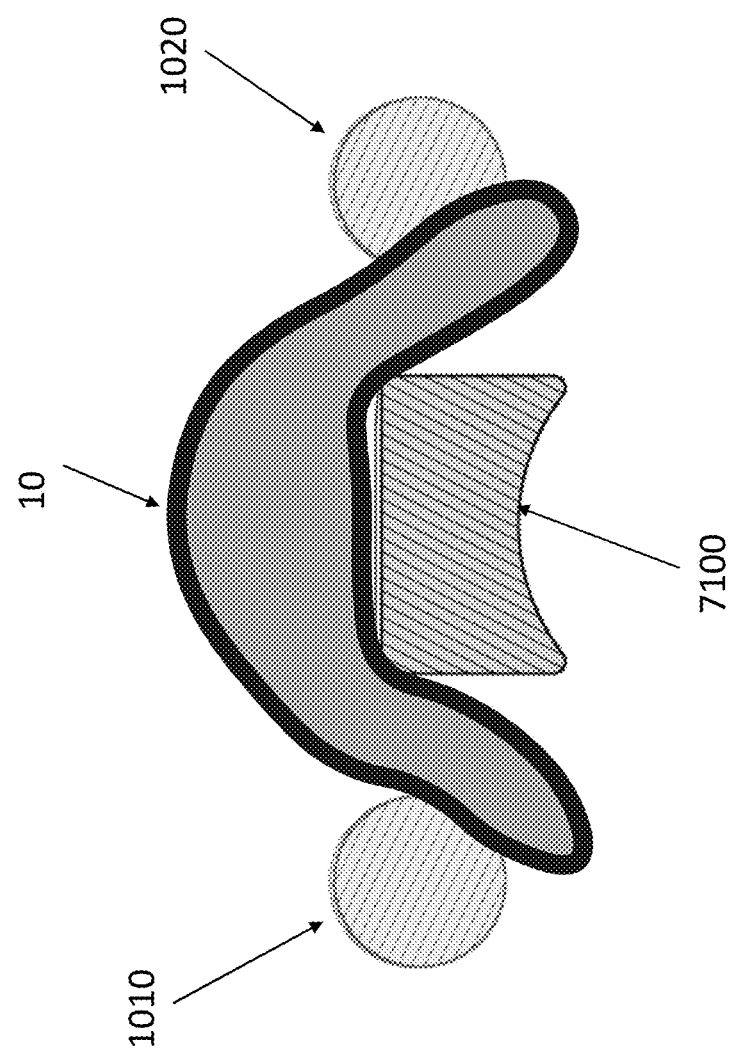
Figure 37:
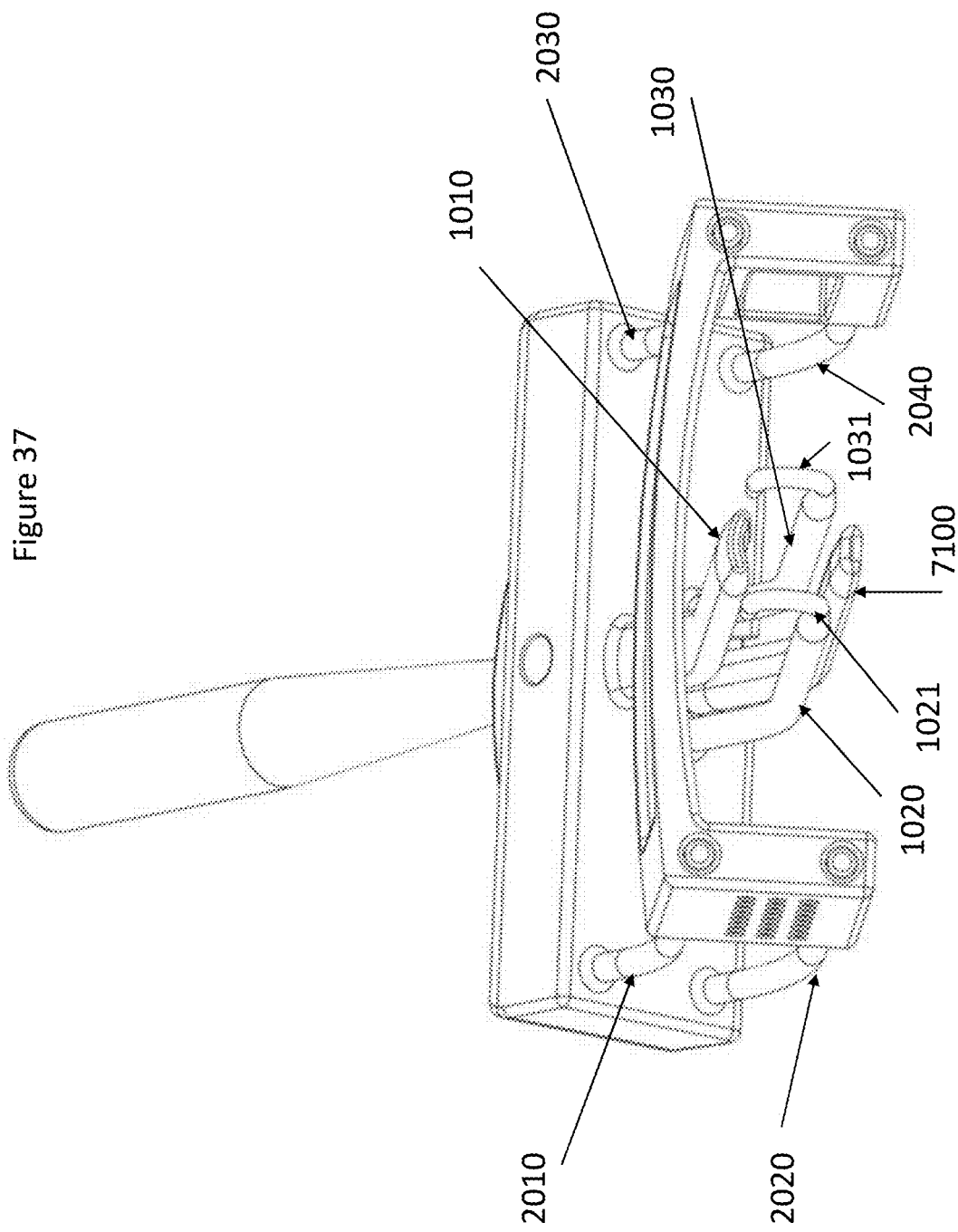
FIGS. 37-38 are additional perspective views of the Achilles tendon repair device, including the shaping rods, clamping member, suture guide and retention hooks.

FIGS. 32-34 show front views of an exemplary embodiment of the device which includes internal and outer rods as well as the clamping arm 7100, with the various views depicting the range of movement of the clamping arm. Likewise, FIGS. 35-36 depict cross sectional views of the tendon 10 being shaped into the curved/draped contour, thereby increasing the surface area in the AP plane, by the pressing (down in the Figure, or in the anterior direction relative to the patient) by internal rods 1010, 1020, while simultaneously being clamped by clamping arm 7100 which moves in the opposite (upward or posterior direction) to securely retain the tendon and further impart the desired contour.

In accordance with another aspect of the disclosure, suture hooks 1021, 1031 can be included at the ends of the internal rods 1020, 1030 respectively. These hooks can curve upward to engage the sutures as the device is being withdrawn from the patient. In some embodiments, the sutures are entirely removed from the patient, yet in other embodiments the sutures are only partially removed upon withdrawal of the device. In the exemplary embodiment shown, the suture hooks 1021, 1031 curve upwardly and back inwardly toward the handle (e.g. approximately 270 degrees). This allows for the sutures to be securely retained on the hooks without falling off/loose as the device is manipulated (e.g. tilted and/or twisted) by the physician as they remove the device from the user. These hooks 1021, 1031 are able to releasably capture the main sutures, as well as loop sutures (as shown in FIGS. 15-18C) and shuttle the sutures, as desired by the physician, to complete the Achilles tendon repair operation. An advantage of the arcuate ends of suture hooks 1021 and 1031 is that these blunt structures prevent undesired piercing/tearing of paratenon upon insertion into a patient. In some embodiments, as the device is removed from the patient, the suture hooks can capture and remove the sutures simultaneously.

Figure 38:
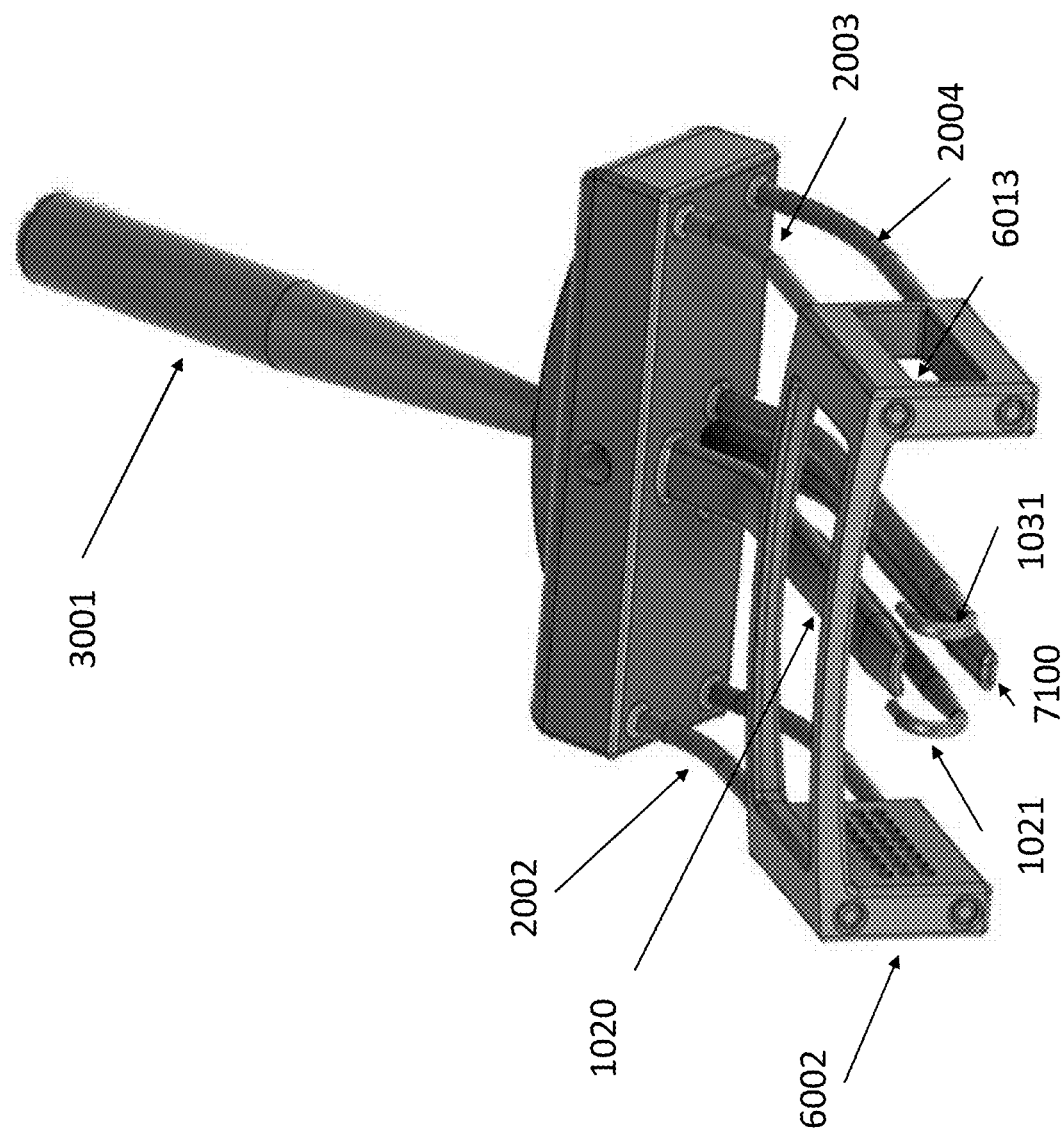

FIG. 38 depicts the Achilles tendon repair device disclosed herein with the clamping arm 7100 vertically aligned with the inner rod 1020 which together "sandwich" or clamp on the anterior and posterior surfaces of the Achilles tendon, respectively. Also, the clamp arm and/or inner rod 1020 can be operated to move up/down via twisting of the handle portion 3001. This movement can occur in tandem, or independently from each other. Also shown are outer rods 2001-2004, with the slidable suture guide 6002 disposed thereon (the suture guide including an opening/window 6013 on the side and top, and suture guides 6030 in its medial sidewall).

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. An Achilles tendon repair device comprising:
a handle having a first end and a second end, defining a length along a longitudinal axis therebetween;
a base, the base having a posterior side, an anterior side, a lateral side, a medial side, a proximal side and a distal side, the first end of the handle coupled to the distal side of the base, the handle extending along the longitudinal axis;
a first set of rods extending from the base,
the first set of rods distributed in an arcuate pattern about the base,
at least one rod of the first set of rods configured to removably engage a posterior surface of a tendon, the at least one rod of the first set of rods configured to extend parallel to the tendon;
a suture needle housing guide, the suture needle housing guide having opposing sidewalls, at least one sidewall configured to receive a suture needle;
a second set of rods extending from the base, the second set of rods configured to receive the suture needle housing guide,
the second set of rods including at least one pair of rods extending parallel to each other and spaced from the first set of rods, and
at least one pair of the second rods being aligned about an axis extending in a posterior-anterior plane.

2. The device of claim 1, wherein the first set of rods includes a first rod, a second rod, a third rod, and a fourth rod equidistantly spaced from each other, with the first rod and fourth rod disposed proximate an anterior edge of the base, and the second rod and third rod disposed proximate a posterior edge of the base.

3. The device of claim 2, wherein the first and fourth rod are aligned along a lateral-medial plane.

4. The device of claim 2, wherein the second and third rod are aligned along a lateral-medial plane.

5. The device of claim 1, wherein each rod of the first set of rods is configured to engage the tendon and drape the tendon into a generally arcuate shape in a posterior-anterior plane.

6. The device of claim 1, wherein the second set of rods includes two pairs of rods, a first pair disposed proximate a lateral edge of the base, a second pair disposed proximate a medial edge of the base.

7. The device of claim 1, wherein the first set of rods are fixedly attached to the base.

8. The device of claim 1, wherein the second set of rods are fixedly attached to the base.

9. The device of claim 1, further comprising wherein the suture needle housing guide is configured as a generally rectangular structure with opposing sidewalls, each sidewall including at least one aperture for receiving the suture needle.

10. The device of claim 9, wherein the suture needle housing guide is configured to be slidingly attached to the second set of rods, the suture needle housing guide including a viewing window on a posterior surface of the suture needle housing guide.

11. The device of claim 1, the arcuate pattern having concavity directed toward the anterior side of the base.

12. An Achilles tendon repair device comprising:
   a handle having a first end and a second end, defining a length along a longitudinal axis therebetween;
   a base, the base having a posterior side, an anterior side, a lateral side, a medial side, a proximal side and a distal side, the first end of the handle coupled to the distal side of the base, the handle extending along the longitudinal axis;
   a first set of rods extending from the base,
      the first set of rods distributed in an arcuate pattern about the base,
      at least one rod of the first set of rods configured to engage a posterior surface of a tendon, the at least one rod of the first set of rods configured to extend parallel to the tendon;
   a suture needle housing guide, the suture needle housing guide having opposing sidewalls, at least one sidewall configured to receive a suture needle;
   a second set of rods extending from the base, the second set of rods configured to receive the suture needle housing guide,
      the second set of rods including at least one pair of rods extending parallel to each other and spaced from the first set of rods; and
      at least one pair of the second rods being aligned about an axis extending in a posterior-anterior plane; and
   wherein at least one of the first set of rods, or the second set of rods, is adjustable;
   a clamping mechanism,
      the clamping mechanism coupled to the base and including a clamp arm configured for displacement in the anterior-posterior plane to engage an anterior surface of the tendon.

13. The device of claim 12, wherein the clamp arm has a radius of curvature.

14. The device of claim 12, wherein the clamp arm has an arcuate cross-sectional shape.

15. The device of claim 12, wherein the clamp arm has convex surface configured to engage the tendon.

16. The device of claim 12, wherein a distal end of clamp arm includes a tapered tip.

17. The device of claim 12, wherein the clamp arm is configured to engage the tendon in tandem with the at least one rod of the first set of rods.

18. The device of claim 12, wherein the clamp arm is positioned along a central longitudinal axis of the claiming mechanism.

19. The device of claim 12, wherein the clamp arm is aligned with at least one of the first rods in the anterior-posterior plane.

20. The device of claim 12, further comprising wherein the suture needle housing guide is configured as a generally rectangular structure with opposing sidewalls, each sidewall including at least one aperture for receiving the suture needle.

21. The device of claim 20, wherein the suture needle housing guide includes a viewing window on a posterior surface of the suture needle housing guide.

* * * * *